(12) United States Patent
Endo

(10) Patent No.: US 11,596,293 B2
(45) Date of Patent: Mar. 7, 2023

(54) ENDOSCOPE SYSTEM AND OPERATION METHOD THEREFOR

(71) Applicant: FUJIFILM Corporation, Tokyo (JP)

(72) Inventor: Maiko Endo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 345 days.

(21) Appl. No.: 16/994,920

(22) Filed: Aug. 17, 2020

(65) Prior Publication Data

US 2020/0375439 A1 Dec. 3, 2020

Related U.S. Application Data

(63) Continuation of application No. PCT/JP2019/003443, filed on Jan. 31, 2019.

(30) Foreign Application Priority Data

Feb. 22, 2018 (JP) .............................. JP2018-029495

(51) Int. Cl.
*A61B 1/00* (2006.01)
*A61B 1/045* (2006.01)
*A61B 1/06* (2006.01)
*A61B 1/313* (2006.01)

(52) U.S. Cl.
CPC ...... *A61B 1/0005* (2013.01); *A61B 1/000095* (2022.02); *A61B 1/045* (2013.01); *A61B 1/0638* (2013.01); *A61B 1/3137* (2013.01)

(58) Field of Classification Search
CPC .................................................. A61B 1/3137
See application file for complete search history.

(56) References Cited

U.S. PATENT DOCUMENTS 5,436,655 A * 7/1995 Hiyama ............. A61B 1/00194
348/45
5,940,126 A * 8/1999 Kimura ............. A61B 1/00181
348/E5.028

(Continued)

FOREIGN PATENT DOCUMENTS

JP 2003-088498 A 3/2003
JP 2004-321244 A 11/2004

(Continued)

OTHER PUBLICATIONS

International Search Report issued in PCT/JP2019/003443; dated Apr. 2, 2019.
Written Opinion issued in PCT/JP2019/003443; dated Apr. 2, 2019.

*Primary Examiner* — John P Leubecker
*Assistant Examiner* — Jae Woo
(74) *Attorney, Agent, or Firm* — Studebaker & Brackett PC

(57) ABSTRACT

In an endoscope system, a frame adjustment unit makes a frame adjustment for changing the number of frames to be displayed per unit time (frame rate) for a normal image and for a computational image on the basis of a computational processing time detected by a computational processing time detection unit and an amount of motion detected by a motion detection unit. A display control unit determines a display method for the normal image and the computational image on the basis of the amount of motion, and the normal image and the computational image are displayed on a monitor in accordance with the display method.

15 Claims, 15 Drawing Sheets

(56) References Cited

U.S. PATENT DOCUMENTS

| | | | | |
|---|---|---|---|---|
| 6,364,829 B1* | 4/2002 | Fulghum | ............. | A61B 1/0669 |
| | | | | 600/178 |
| 6,498,948 B1* | 12/2002 | Ozawa | ............... | G01B 9/02003 |
| | | | | 600/478 |
| 9,649,018 B2* | 5/2017 | Morimoto | ............ | A61B 1/0646 |
| 2003/0030722 A1* | 2/2003 | Ozawa | .................. | H04N 9/735 |
| | | | | 348/71 |
| 2007/0216781 A1* | 9/2007 | Miyanohara | ........... | H04N 19/51 |
| | | | | 348/E5.065 |
| 2008/0051642 A1* | 2/2008 | Krupnik | ................. | A61B 1/041 |
| | | | | 600/302 |
| 2008/0119691 A1* | 5/2008 | Yagi | ...................... | A61B 1/042 |
| | | | | 600/109 |
| 2012/0101348 A1* | 4/2012 | Yamaguchi | ......... | A61B 1/0646 |
| | | | | 600/109 |
| 2012/0157775 A1 | 6/2012 | Yamaguchi | | |
| 2015/0238086 A1* | 8/2015 | Saito | .................. | A61B 1/00006 |
| | | | | 600/339 |
| 2018/0310812 A1* | 11/2018 | Kuriyama | .......... | A61B 1/00009 |
| 2020/0077897 A1* | 3/2020 | Saeki | ................ | G01N 29/0672 |
| 2021/0282630 A1* | 9/2021 | Kikuchi | ............... | H04N 5/2354 |
| 2021/0307587 A1* | 10/2021 | Iwasaki | ............... | A61B 1/0655 |

FOREIGN PATENT DOCUMENTS

| | | |
|---|---|---|
| JP | 2011-36488 A | 2/2011 |
| JP | 2012-090725 A | 5/2012 |
| JP | 2012-130429 A | 7/2012 |
| JP | 2014-128423 A | 7/2014 |

* cited by examiner

ENDOSCOPE SYSTEM AND OPERATION METHOD THEREFOR

CROSS-REFERENCE TO RELATED APPLICATIONS

This application is a Continuation of PCT International Application No. PCT/JP2019/003443 filed on 31 Jan. 2019, which claims priority under 35 U.S.C § 119(a) to Japanese Patent Application No. 2018-029495 filed on 22 Feb. 2018. The above application is hereby expressly incorporated by reference, in its entirety, into the present application.

BACKGROUND OF THE INVENTION

1. Field of the Invention

The present invention relates to an endoscope system and an operation method therefor with which a normal image and a computational image are simultaneously displayed while an uneasy feeling resulting from a delay of the computational image and motion of the photographic subject is relieved.

2. Description of the Related Art

In the medical field, it is a common practice to make diagnoses using an endoscope system that includes a light source device, an endoscope, and a processor device. Specifically, in a normal case, white light is used as illumination light to capture an image of an observation target and obtain and display an image (hereinafter referred to as a normal image) with which the observation target can be observed in natural colors. Meanwhile, an endoscope system is widely used that not only captures an image of an observation target as a normal image but also controls the wavelength of illumination light to be radiated onto the observation target and performs signal processing, such as spectral estimation processing, for image signals obtained by image capturing of the observation target, thereby obtaining an observation image in which a specific tissue or structure, such as a blood vessel or a glandular tubular structure, is highlighted.

Currently, a technique is being studied in which biological function information is measured on the basis of image signals obtained by image capturing of an observation target, and the biological function information is used at the time of diagnosis. For example, it is known that a lesion, such as a cancer, is in a low-oxygen state. Therefore, of the biological function information, the oxygen saturation level is measured and used in a diagnosis to thereby facilitate detection of the lesion.

The biological function information, such as the oxygen saturation level, is measured by performing image processing in which computation of image signals is performed. A normal image and a computational image that represents, for example, the results of measurement of the biological function information obtained by computation of the image signals are sometimes compared with each other for a more correct diagnosis. For displaying such normal image and computational image, the following techniques are disclosed.

For example, an endoscope system is disclosed that performs advanced image processing via a network, causes a local image processing unit to perform image processing for generating an observation image, and combines the results of the processing to generate a display image (JP2014-128423A). Further, an electronic endoscope system is disclosed that stores an image capture signal obtained by using normal light and an image capture signal obtained by using special light in separate storage means and obtains the image capture signals from the respective storage means for display in accordance with a specific timing signal (JP2004-321244A). Further, an electronic endoscope system is disclosed that includes an electronic endoscope, a processor, and an image processing apparatus and in which the image processing apparatus outputs information regarding a first image processing time to the processor and the processor controls on the basis of the image processing time the timing at which a second video signal is output (JP2011-36488A).

SUMMARY OF THE INVENTION

According to JP2014-128423A, JP2004-321244A, and JP2011-36488A, a normal image and a computational image are displayed while display of the normal image is delayed so as to be in synchronization with the computational image. However, computation having a heavy calculation load may lead to a decrease in the frame rate of the computational image. In this case, specifically, in a case where motion of the photographic subject becomes large, for synchronous display of the computational image with the normal image, the frame rate may be insufficient relative to the motion of the photographic subject.

An object of the present invention is to provide an endoscope system and an operation method therefor with which a normal image and a computational image are simultaneously displayed while an uneasy feeling resulting from a delay of the computational image or motion of the photographic subject is relieved.

An endoscope system according to the present invention includes an image obtaining unit, a computational image generation unit, a normal image generation unit, a computational processing time detection unit, a motion detection unit, a frame adjustment unit, a display control unit, and a display unit. The image obtaining unit obtains a plurality of images obtained by radiating a plurality of types of illumination light in different wavelength ranges to a photographic subject to capture images of the photographic subject. The computational image generation unit generates a computational image by performing computational processing for at least one image among the plurality of images. The normal image generation unit generates a normal image by not performing the computational processing for at least one image among the plurality of images. The computational processing time detection unit detects a computational processing time taken to generate the computational image. The motion detection unit detects an amount of relative motion of the photographic subject. The frame adjustment unit makes a frame adjustment for changing the number of frames to be displayed per unit time for the normal image and/or the computational image. The display control unit determines a display method for the normal image and the computational image subjected to the frame adjustment on the basis of the computational processing time and the amount of motion. The display unit displays the normal image and the computational image in accordance with the display method.

It is preferable that the display method be a method in which display of the normal image is delayed by the computational processing time.

It is preferable that the frame adjustment be a process for decreasing the number of frames to be displayed per unit time for the normal image.

It is preferable that the frame adjustment be a process for increasing the number of frames to be displayed per unit time for the computational image.

It is preferable that the frame adjustment be a process for increasing the number of frames to be displayed per unit time for the computational image by replicating the computational image.

It is preferable that the frame adjustment be a process for decreasing a difference between the number of frames to be displayed per unit time for the computational image and the number of frames to be displayed per unit time for the normal image.

It is preferable that the motion detection unit detect a relative motion vector of the photographic subject, and the frame adjustment be a process for generating an interpolation frame for the computational image on the basis of the motion vector.

It is preferable that the computational image generation unit generate computational images by using at least one image among the plurality of images twice or more in the computational processing to generate at least two computational images.

It is preferable that the display method be a method in which in a case where the amount of motion is equal to or larger than a threshold value, the normal image and the computational image are displayed in such a manner that a display area of the normal image is equal to or larger than a display area of the computational image, and in a case where the amount of motion is smaller than the threshold value, the normal image and the computational image are displayed in such a manner that the display area of the computational image is equal to or larger than the display area of the normal image.

It is preferable that the display unit include at least one monitor.

It is preferable that the display method be a method in which the computational image is superimposed on the normal image and displayed.

It is preferable that the display unit include at least two monitors; the monitors each include a line-of-sight detection device that detects a line of sight of an observer; the line-of-sight detection device include a line-of-sight movement detection unit that detects a line-of-sight movement time taken for the movement; and in a case where the line of sight of the observer moves from one of the monitors that displays the computational image to the other monitor that displays the normal image, the display control unit determine the display method for the computational image and the normal image on the basis of the line-of-sight movement time.

It is preferable that the display method be a method in which display of the normal image is delayed by the line-of-sight movement time.

It is preferable that the computational processing be computational processing for generating an oxygen saturation image.

It is preferable that the computational processing be computational processing for generating a blood vessel highlight image.

An operation method for an endoscope system according to the present invention includes: a step of obtaining, by an image obtaining unit, a plurality of images obtained by radiating a plurality of types of illumination light in different wavelength ranges to a photographic subject to capture images of the photographic subject; a step of generating, by a computational image generation unit, a computational image by performing computational processing for at least one image among the plurality of images; a step of generating, by a normal image generation unit, a normal image by not performing the computational processing for at least one image among the plurality of images; a step of detecting, by a computational processing time detection unit, a computational processing time taken to generate the computational image; a step of detecting, by a motion detection unit, an amount of relative motion of the photographic subject; a step of making, by a frame adjustment unit, a frame adjustment for changing the number of frames to be displayed per unit time for the normal image and/or the computational image; a step of determining, by a display control unit, a display method for the normal image and the computational image subjected to the frame adjustment on the basis of the computational processing time and the amount of motion; and a step of displaying, by a display unit, the normal image and the computational image in accordance with the display method.

With the endoscope system and the operation method therefor according to the present invention, a normal image and a computational image are simultaneously displayed while an uneasy feeling resulting from a delay of the computational image or motion of the photographic subject is relieved.

DESCRIPTION OF THE PREFERRED EMBODIMENTS

First Embodiment

Figure 1:
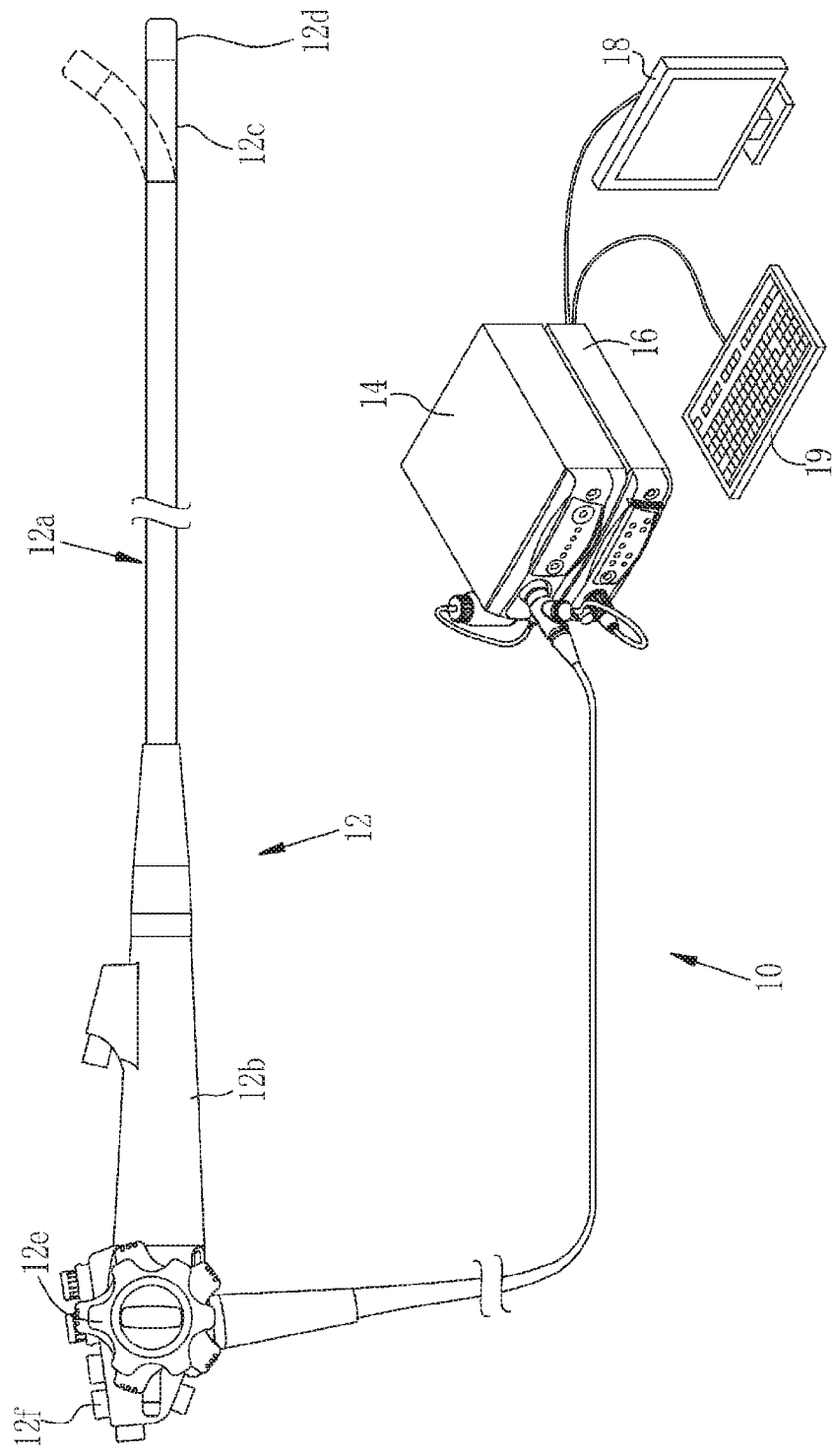
FIG. 1 is an external view of an endoscope system.

In FIG. 1, an endoscope system 10 has an endoscope 12, a light source device 14, a processor device 16, a monitor 18, and a console 19. The endoscope 12 is optically connected to the light source device 14 and electrically connected to the processor device 16. The endoscope 12 has an insertion part 12a that is inserted in the interior of the body that is an observation target, an operation part 12b that is provided at the proximal end portion of the insertion part 12a, and a bending part 12c and a distal end part 12d that are provided on the distal end side of the insertion part 12a. The bending part 12c makes a bending motion in response to an operation of an angle knob 12e of the operation part 12b. The distal end part 12d is turned in an intended direction in association with the bending motion of the bending part 12c.

Note that the endoscope system 10 has a plurality of observation modes among which the types of images to be displayed differ. As the observation modes, three types, namely, a normal mode, an oxygen saturation mode, and a multi-observation mode, are provided. In the normal mode, a natural-color normal image obtained by image capturing of an observation target using white light as illumination light is displayed on the monitor 18. In the oxygen saturation mode, an image of oxygen saturation level measurement representing the results of measurement of biological functions is displayed on the monitor 18 on the basis of a first image and a second image in different wavelength ranges. This image is an image (hereinafter referred to as an oxygen saturation image) obtained by measuring the oxygen saturation level of an observation target and representing the measured oxygen saturation level by an image using pseudo colors, etc. by using correlations among the first image, the second image, and oxygen saturation levels. In the multi-observation mode, switching between the normal mode and the oxygen saturation mode is automatically performed. That is, in the multi-observation mode, a normal image in the normal mode and an oxygen saturation image in the oxygen saturation mode are displayed without manually switching between the observation modes. Note that in the multi-observation mode, a blood vessel highlight mode in which a blood vessel highlight image is displayed on the monitor 18 may be performed instead of the oxygen saturation mode. In this case, switching between the normal mode and the blood vessel highlight mode is automatically performed. It is preferable to generate a blood vessel highlight image by performing blood vessel highlight computation between a plurality of images obtained by using multi-frame illumination that is used in the blood vessel highlight mode. Here, mainly, computation between images of a plurality of frames, such as oxygen saturation level computation for measuring an oxygen saturation level and blood vessel highlight computation, is called computational processing. An image generated by performing the computational processing is called a computational image.

In the endoscope system 10, other observation modes can be used in addition to the multi-observation mode, the normal mode, and the oxygen saturation mode. Switching between the observation modes is performed by a mode switching switch (hereinafter referred to as a mode switching SW) 12f that is a scope switch provided at the operation part 12b of the endoscope. With the mode switching SW 12f, switching between a plurality of types of illumination light can be manually performed. The observation mode assumed in this embodiment is the multi-observation mode.

The processor device 16 is electrically connected to the monitor 18 and the console 19. The monitor 18 outputs and displays image information, etc. FIG. 1 illustrates only one monitor 18; however, the number of connected monitors 18 is not limited to one, and two or more monitors 18 may be connected. The console 19 functions as a UI (user interface) that accepts operations of inputting functional settings, etc. Note that to the processor device 16, an external recording unit (not illustrated) for recording image information, etc. may be connected.

Figure 2:
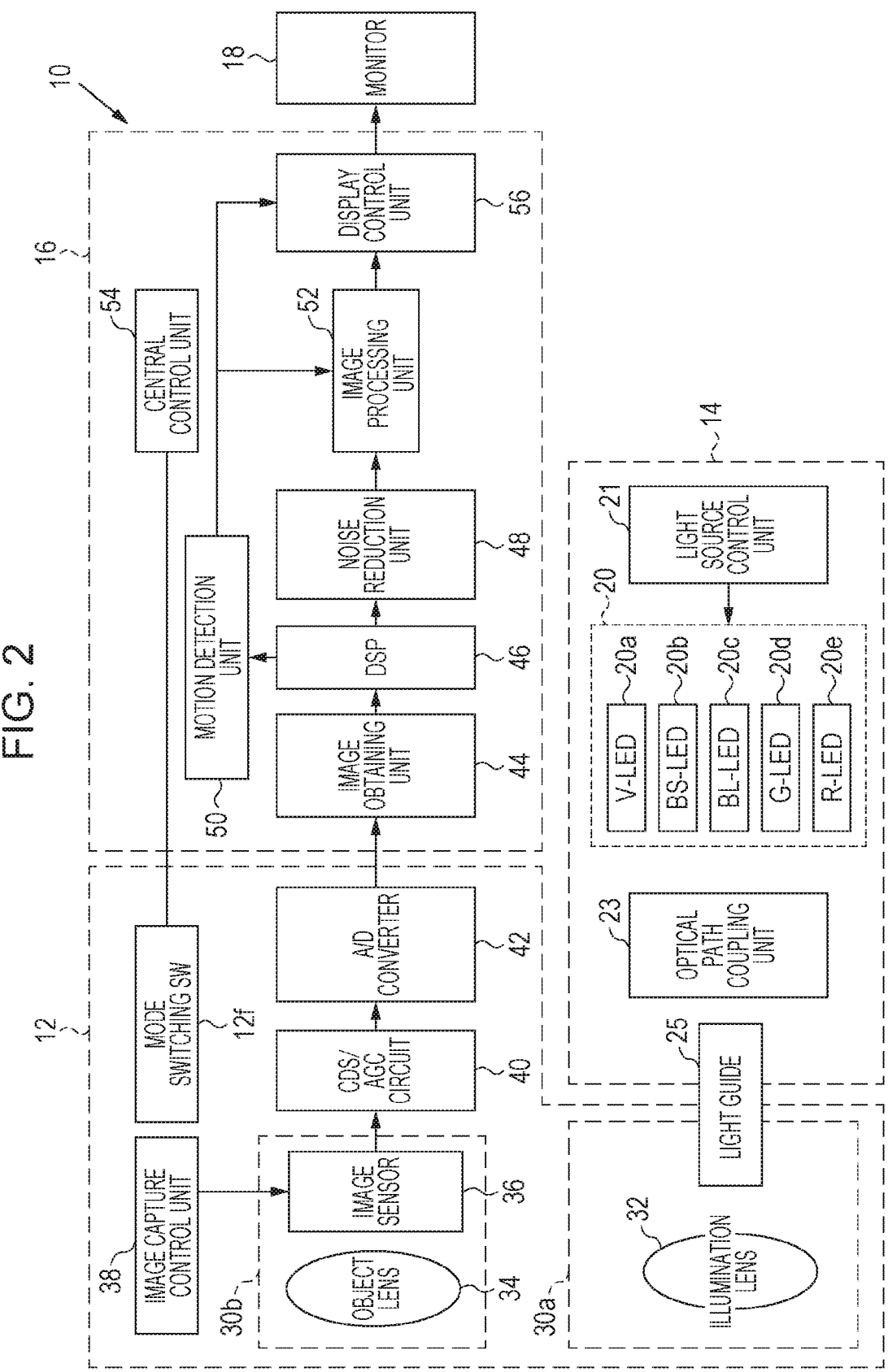
FIG. 2 is a block diagram illustrating functions of an endoscope system according to a first embodiment.

As illustrated in FIG. 2, the light source device 14 includes a light source 20 and a light source control unit 21 that controls the light source 20. The light source 20 has, for example, a plurality of semiconductor light sources, and these light sources are each turned on or off. In a case of turn-on, the amount of light emission of each semiconductor light source is controlled to emit illumination light with which an observation target is illuminated. In this embodiment, the light source 20 has LEDs of five colors, namely, a V-LED (Violet Light Emitting Diode) 20a, a BS-LED (Blue Short-wavelength Light Emitting Diode) 20b, a BL-LED (Blue Long-wavelength Light Emitting Diode) 20c, a G-LED (Green Light Emitting Diode) 20d, and an R-LED (Red Light Emitting Diode) 20e.

The V-LED 20a emits violet light V in a wavelength range of 405±10 nm. The BS-LED 20b emits first blue light BS in a wavelength range of 450±10 nm. The BL-LED 20c emits second blue light BL in a wavelength range of 470±10 nm. The G-LED 20d emits green light G in a wavelength range of 540±10 nm. The R-LED 20e emits red light R in a wavelength range of 640±20 nm. Note that the center wavelength and the peak wavelength of each of the LEDs 20a to 20e may be the same or may be different.

The light source control unit 21 inputs control signals to the LEDs 20a to 20e individually to control, for example, turn-on or turn-off of the LEDs 20a to 20e or the amounts of light emission thereof at the time of turn-on individually. Control for turn-on or turn-off by the light source control unit 21 differs among the modes. For obtaining a normal image, the BS-LED 20b, the G-LED 20d, and the R-LED 20e are simultaneously turned on to emit the first blue light BS, the green light G, and the red light R simultaneously. The V-LED 20a may be simultaneously turned on in addition to these LEDs to thereby emit the violet light V simultaneously. For obtaining an oxygen saturation image, switching is performed between a first measurement light emission mode in which the BL-LED 20c is turned on to emit the second blue light BL and a second measurement light emission mode in which the BS-LED 20b, the G-LED 20d, and the R-LED 20e are simultaneously turned on to emit the first blue light BS, the green light G, and the red light R simultaneously. Light emission in the second measurement light emission mode for obtaining an oxygen saturation image and light emission for obtaining a normal image are the same. Therefore, in the multi-observation mode in which a normal image and an oxygen saturation image are automatically obtained, the first measurement light emission mode and the second measurement light emission mode for obtaining an oxygen saturation image are alternately repeated. Then, an image captured in the second measurement light emission mode for obtaining an oxygen saturation image is used also as an image for a normal image.

Light emitted from each of the LEDs 20a to 20e enters a light guide 25 via an optical path coupling unit 23 constituted by a mirror, a lens, etc. The light guide 25 is built in the endoscope 12 and in a universal cord (a cord that connects the endoscope 12 with the light source device 14 and the processor device 16). Light from the optical path coupling unit 23 propagates through the light guide 25 up to the distal end part 12d of the endoscope 12.

In the distal end part 12d of the endoscope 12, an illumination optical system 30a and an image capture optical system 30b are provided. The illumination optical system 30a has an illumination lens 32, and illumination light propagating through the light guide 25 passes through the illumination lens 32 and is radiated onto an observation target. The image capture optical system 30b has an object lens 34 and an image sensor 36. Light from an observation target resulting from radiation of illumination light is incident on the image sensor 36 via the object lens 34. Accordingly, an image of the observation target is formed on the image sensor 36.

The image sensor 36 is a color image sensor used to capture images of an observation target that is being illuminated with illumination light. As each pixel of the image sensor 36, a B pixel (blue pixel) having a B (blue) color filter, a G pixel (green pixel) having a G (green) color filter, or an R pixel (red pixel) having an R (red) color filter is provided. The B color filter mainly allows light in a blue-color range, specifically, light in a wavelength range of 380 to 560 nm, to pass therethrough. The peak wavelength at which the transmittance reaches its peak exists near 460 to 470 nm. The G color filter mainly allows light in a green-color range, specifically, light in a wavelength range of 450 to 630 nm, to pass therethrough. The R color filter mainly allows light in a red-color range, specifically, light in a wavelength range of 580 to 760 nm, to pass therethrough.

As the image sensor 36, a CCD (Charge Coupled Device) image sensor or a CMOS (Complementary Metal-Oxide Semiconductor) image sensor can be used. Instead of the image sensor 36, which is a primary-color image sensor, a complementary-color image sensor including complementary-color filters of C (cyan), M (magenta), Y (yellow), and G (green) may be used. In a case of using a complementary-color image sensor, image signals for four colors of C, M, Y, and G are output. Therefore, color conversion from complementary colors to primary colors is performed to convert the image signals for four colors of C, M, Y, and G to image signals for three colors of R, G, and B, so that image signals for respective colors of R, G, and B can be obtained as in the case of using the image sensor 36.

The image sensor 36 is driven and controlled by an image capture control unit 38. Control by the image capture control unit 38 differs among the modes. In the multi-observation mode, the normal mode and the oxygen saturation mode are repeated. As described above, in the normal mode and in the second measurement light emission mode of the oxygen saturation mode, the same image can be used. Therefore, actually, the first measurement light emission mode and the second measurement light emission mode of the oxygen saturation mode are alternately repeated to obtain images for a normal image and for an oxygen saturation image.

Specifically, in the oxygen saturation mode, the image capture control unit 38 controls the image sensor 36 to perform alternate switching between a first measurement image capture mode in which image capturing of an observation target that is being illuminated with the second blue light BL in the first measurement light emission mode is performed for one frame and a second measurement image capture mode in which image capturing of the observation target that is being illuminated with the first blue light BS, the green light G, and the red light R in the second measurement light emission mode is performed for one frame. Accordingly, in the first measurement image capture mode, a B1 image signal is output from each B pixel of the image sensor 36, a G1 image signal is output from each G pixel thereof, and an R1 image signal is output from each R pixel thereof. Further, in the second measurement image capture mode, a B2 image signal is output from each B pixel of the image sensor 36, a G2 image signal is output from each G pixel thereof, and an R2 image signal is output from each R pixel thereof. In the normal mode, the image signals output in the second measurement image capture mode are used.

Image signals output from the image sensor 36 are transmitted to a CDS/AGC circuit 40. The CDS/AGC (Correlated Double Sampling/Automatic Gain Control) circuit 40 performs correlated double sampling (CDS) or automatic gain control (AGC) for analog image signals obtained from the image sensor 36. The image signals that pass through the CDS/AGC circuit 40 are converted to digital image signals by an A/D (Analog/Digital) converter 42. The digital image signals after A/D conversion are input to the processor device 16.

The processor device 16 includes an image obtaining unit 44, a DSP (Digital Signal Processor) 46, a noise reduction unit 48, a motion detection unit 50, an image processing unit 52, a central control unit 54, and a display control unit 56. The central control unit 54 detects the operation of the mode switching SW 12f, and controls each unit of the processor device 16 according to the selected observation mode. The image obtaining unit 44 receives image signals input from the endoscope 12 and transmits the received image signals to the DSP 46.

The DSP 46 performs various types of signal processing including defect correction, offsetting, gain correction, linear matrix processing, gamma conversion, demosaicing, and YC conversion for the received image signals. In the defect correction, signals from defective pixels of the image sensor 36 are corrected. In the offsetting, a dark current component is removed from the image signals subjected to the defect correction, and an accurate zero level is set. In the gain correction, the image signals of respective colors after the offsetting are multiplied by specific gains to adjust the signal level of each image signal. For the image signals of respective colors after the gain correction, linear matrix processing for increasing color reproducibility is performed.

Thereafter, gamma conversion is performed to adjust the brightness or saturation of each image signal. The image signals after the linear matrix processing are subjected to demosaicing (also called isotropic processing or synchronization processing) to generate, for each pixel, signals of missing colors by interpolation. With the demosaicing, every pixel has signals of the respective colors of R, G, and B. The DSP 46 performs the YC conversion on each image signal after the demosaicing and outputs brightness signals Y, color difference signals Cb, and color difference signals Cr to the noise reduction unit 48.

The noise reduction unit 48 performs noise reduction processing using, for example, a moving average method or a median filter method for the image signals subjected to the demosaicing, etc. in the DSP 46. The image signals in which noise is reduced are input to the image processing unit 52.

Figure 3:
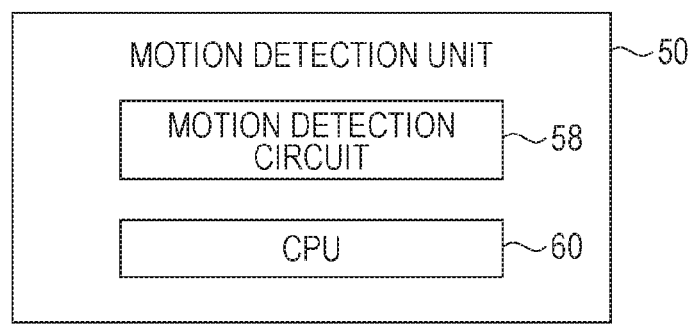
FIG. 3 is a block diagram illustrating functions of a motion detection unit.

The motion detection unit 50 analyzes image signals from the DSP 46 to detect the amount of relative motion of an observation region. As illustrated in FIG. 3, the motion detection unit 50 has a motion detection circuit 58 and a CPU 60. The motion detection circuit 58 has a frame memory that stores image signals from the DSP 46 for two frames before and after an image capture time. For example, a pattern matching method is used to search for pixels, in the images of the two frames, corresponding to the same observation region and detect the spatial distance between the pixels and the direction thereof as a motion vector. Note that a motion vector described herein is a value that includes both the amount of motion and the motion direction. The motion detection circuit 58 outputs to the CPU 60 the amount of relative motion of the observation region obtained from the detected motion vector. The CPU 60 compares the amount of motion with a preset threshold value and sends the result to the image processing unit 52 and the display control unit 56. Here, the amount of relative motion is the amount of relative motion in a specific time and can be obtained from the sum of motion vectors detected in a certain time. As the value of the amount of motion is large, the relative motion of the photographic subject is large. On the other hand, as the value of the amount of motion is small, the relative motion of the photographic subject is small.

Figure 4:
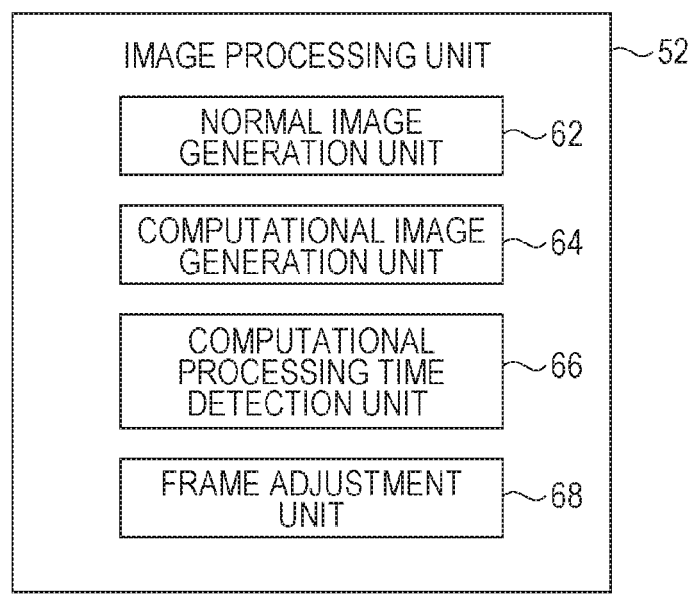
FIG. 4 is a block diagram illustrating functions of an image processing unit.

The image processing unit 52 has a normal image generation unit 62, a computational image generation unit 64, a computational processing time detection unit 66, and a frame adjustment unit 68 as illustrated in FIG. 4. In the image processing unit 52, image signals from the noise reduction unit 48 are sent to any of the normal image generation unit 62 and the computational image generation unit 64 depending on the set mode. In this embodiment, as described above, the multi-observation mode is set, and the normal mode and the oxygen saturation mode are automatically repeated. Specifically, in a case of the oxygen saturation mode, image signals from the noise reduction unit 48 are input to the computational image generation unit 64. In this embodiment, in a case of the second measurement image capture mode in the oxygen saturation mode, image signals from the noise reduction unit 48 are input to the normal image generation unit 62 and the computational image generation unit 64 to thereby also generate an image in the normal mode.

The normal image generation unit 62 performs further processing, namely, color conversion processing including 3×3 matrix processing, gradation transformation, three-dimensional LUT (Look-Up Table) processing, etc., for the input R2 image signals, G2 image signals, and B2 image signals for one frame. The normal image generation unit 62 performs various types of color enhancing processing for RGB image data subjected to the color conversion processing. The normal image generation unit 62 performs structure enhancement processing including spatial frequency enhancement for the RGB image data subjected to the color enhancement processing. The RGB image data subjected to the structure enhancement processing is sent to the display control unit 56 as a normal image. Note that "image data" described herein is used as a synonym for "image signals".

The computational image generation unit 64 uses correlations between oxygen saturation levels and the B1 image signals, the G2 image signals, and the R2 image signals among the image signals obtained in the oxygen saturation mode to calculate oxygen saturation levels. The method for calculating oxygen saturation levels will be described below.

The calculated oxygen saturation levels are represented by an image using pseudo colors, etc. to generate an oxygen saturation image. The oxygen saturation image is sent to the display control unit 56.

The computational processing time detection unit 66 detects the computational processing time from when image signals to be subjected to computation are input to the computational image generation unit 64 to when a computational image is generated. The detected computational processing time is sent to the display control unit 56 for use in determination of the display method for a normal image. The computational processing time may be the average of the times taken for computation of a plurality of images or may be a representative value, such as the time taken for computation of one sample image.

Figure 5:
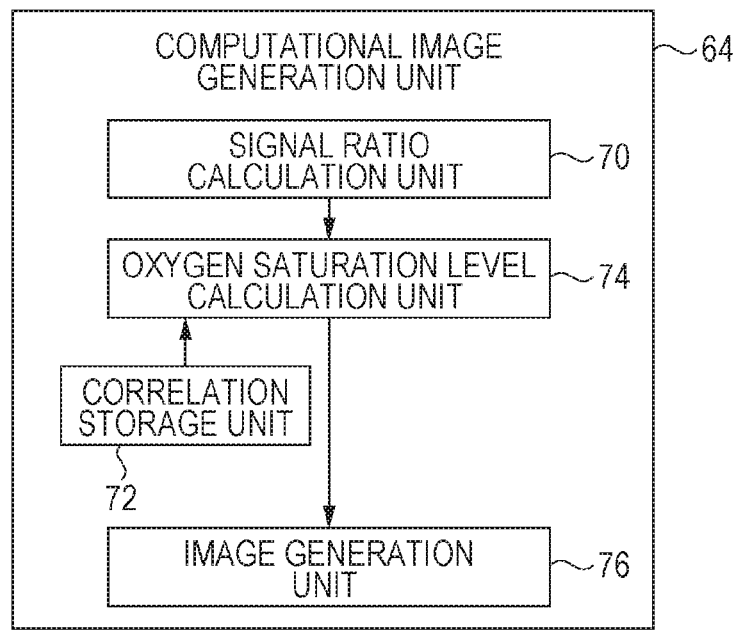
FIG. 5 is a block diagram illustrating functions of a computational image generation unit.

As described above, in this embodiment, a computational image is an oxygen saturation image. As illustrated in FIG. 5, the computational image generation unit 64 includes a signal ratio calculation unit 70, a correlation storage unit 72, an oxygen saturation level calculation unit 74, and an image generation unit 76. The signal ratio calculation unit 70 calculates signal ratios that are used by the oxygen saturation level calculation unit 74 to calculate oxygen saturation levels. Specifically, the signal ratio calculation unit 70 calculates, for each pixel, a signal ratio B1/G2 between the B1 image signal and the G2 image signal, a signal ratio R2/G2 between the R2 image signal and the G2 image signal, and a signal ratio G2/B2 between the G2 image signal and the B2 image signal.

Figure 6:
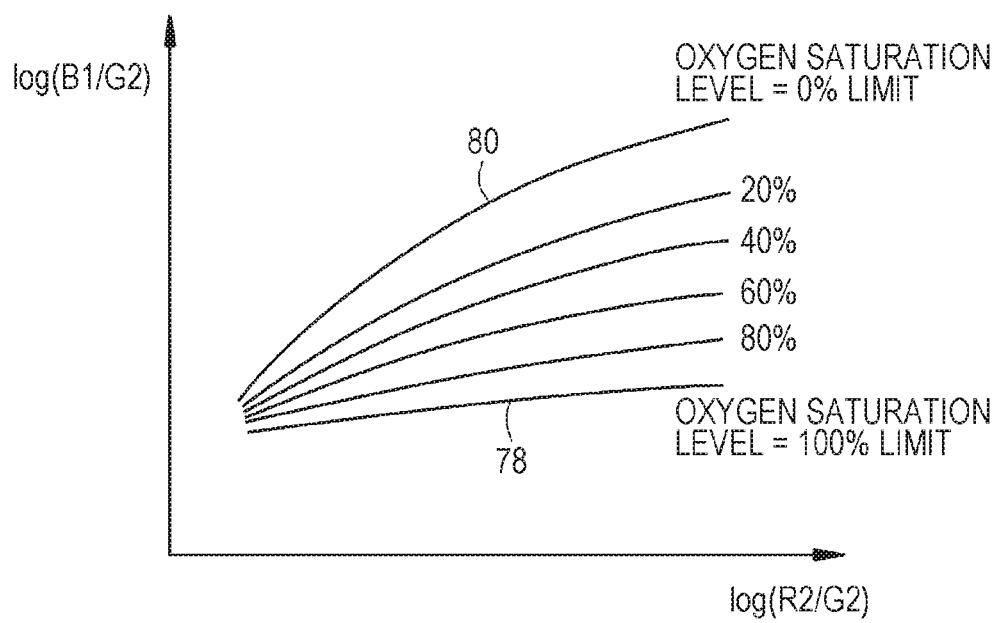
FIG. 6 is a graph illustrating the positions of isopleths of oxygen saturation levels in a first feature space, where the vertical axis represents $\log(B1/G2)$ and the horizontal axis represents $\log(R2/G2)$.

The correlation storage unit 72 stores correlations between the signal ratios calculated by the signal ratio calculation unit 70 and oxygen saturation levels in storage means, such as an LUT (Look-Up Table). In a case where the correlations are expressed in a first feature space defined by the vertical axis representing log(B1/G2) and the horizontal axis representing log(R2/G2), an isopleth that connects portions for which the oxygen saturation levels are the same is formed substantially in the horizontal axis direction in the first feature space as illustrated in FIG. 6. Further, an isopleth for a higher oxygen saturation level is located on a lower side in the vertical axis direction. For example, an isopleth 78 for a 100% oxygen saturation level is located below an isopleth 80 for a 0% oxygen saturation level.

Note that the position and shape of each isopleth in the first feature space can be obtained in advance by a physical simulation of light scattering. Further, the correlation storage unit 72 stores the correlations between the signal ratios B1/G2 and R2/G2 and the oxygen saturation levels; however, the correlation storage unit 72 need not store the correlations with the signal ratios B1/G2 and R2/G2 and may store correlations between first computational values obtained by performing specific computation (for example, difference processing) based on the B1 image signals, the G2 image signals, and the R2 image signals and the oxygen saturation levels.

Figure 7:
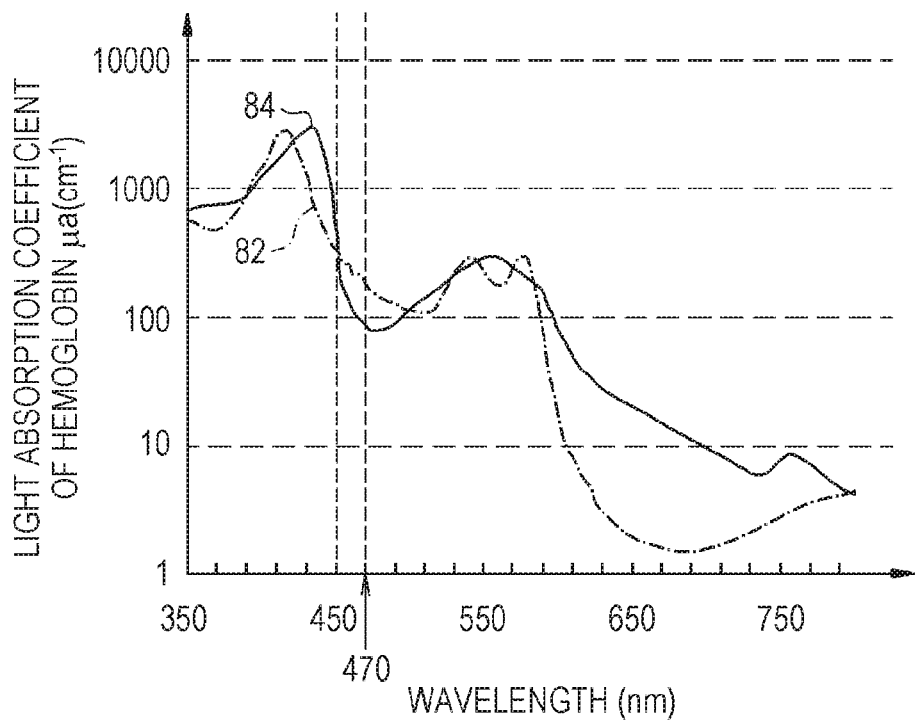
FIG. 7 is a graph illustrating the light absorption coefficient of oxyhemoglobin and that of reduced hemoglobin.

The above-described correlations are closely related to the light absorption characteristics or light scattering characteristics of oxyhemoglobin (graph 82) and reduced hemoglobin (graph 84) illustrated in FIG. 7. For example, in a wavelength range in which the difference in the light absorption coefficient between oxyhemoglobin and reduced hemoglobin is large, such as the wavelength range 470±10 nm of the second blue light BL, the amount of light absorption changes in accordance with the oxygen saturation level of hemoglobin, and therefore, information regarding the oxygen saturation level can be easily handled. Therefore, when the signal ratio B1/G2 involving the B1 image signal corresponding to the second blue light BL having a center wavelength of 470 nm is used, the oxygen saturation level can be calculated. However, the signal ratio B1/G2 not only depends on the oxygen saturation level but also depends on the blood volume to a large degree. Therefore, in addition to the signal ratio B1/G2, the signal ratio R2/G2 that changes mainly in accordance with the blood volume is also used, so that the oxygen saturation level can be accurately obtained without being affected by the blood volume. Note that in a wavelength range of 540±20 nm, which is the wavelength range of green light included in the G2 image signal, the light absorption coefficient of hemoglobin is relatively high, and therefore, the wavelength range of 540±20 nm is a wavelength range in which the amount of light absorption is likely to change in accordance with the blood volume.

Figure 8:
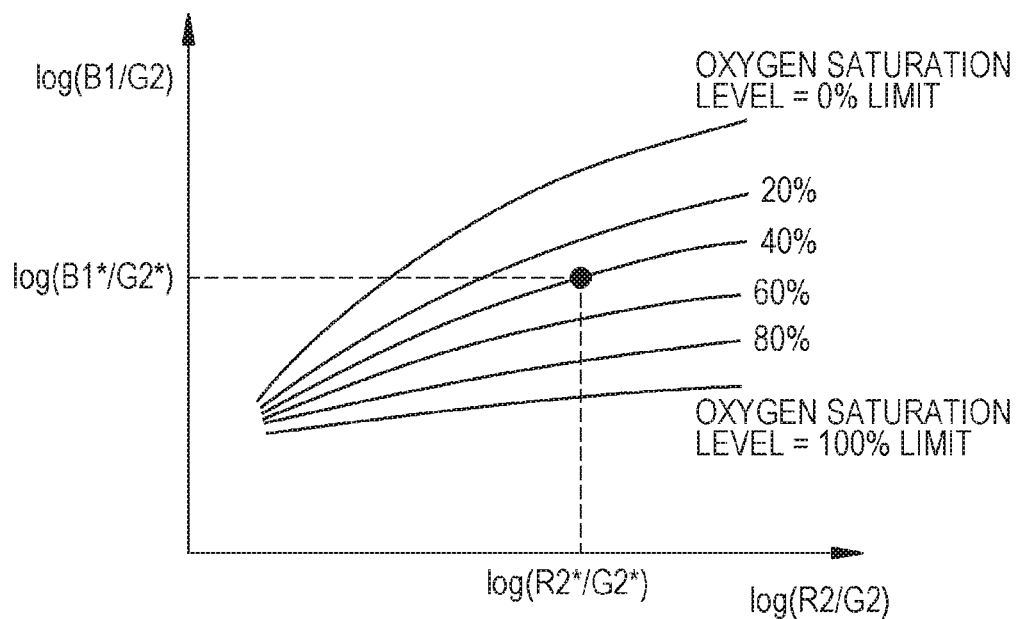
FIG. 8 is a diagram for explaining an oxygen saturation level calculation method.

The oxygen saturation level calculation unit 74 refers to the correlations stored in the correlation storage unit 72 and calculates an oxygen saturation level corresponding to the signal ratios B1/G2 and R2/G2 for each pixel. For example, in a case where the oxygen saturation level calculation unit 74 refers to the correlations stored in the correlation storage unit 72, an oxygen saturation level corresponding to the signal ratios B1*/G2* and R2*/G2* of a specific pixel is "40%" as illustrated in FIG. 8. Therefore, the oxygen saturation level calculation unit 74 calculates the oxygen saturation level as "40%".

Note that there is little chance that the signal ratios B1/G2 and R2/G2 become extremely large or extremely small. That is, there is little chance that the combinations of the values of the signal ratios B1/G2 and R2/G2 are distributed below the isopleth 78 (see FIG. 6) that corresponds to a 100% oxygen saturation level, which is the upper limit, or to the contrary, the combinations are distributed above the isopleth 80 (see FIG. 6) that corresponds to a 0% oxygen saturation level, which is the lower limit. However, in a case where the combinations are distributed below the isopleth 78 that corresponds to the upper limit, the oxygen saturation level is assumed to be 100%, and in a case where the combinations are distributed above the isopleth 80 that corresponds to the lower limit, the oxygen saturation level calculation unit 74 assumes the oxygen saturation level to be 0%. Further, in a case where a point that corresponds to the signal ratios B1/G2 and R2/G2 is not distributed between the isopleth 78 corresponding to the upper limit and the isopleth 80 corresponding to the lower limit, display may be performed so that the low reliability level of the oxygen saturation level at the pixel is known, or the oxygen saturation level need not be calculated.

The image generation unit 76 uses the oxygen saturation levels calculated by the oxygen saturation level calculation unit 74 to generate an oxygen saturation image, which is an image representing the oxygen saturation levels. Specifically, the image generation unit 76 obtains the B2 image signals, the G2 image signals, and the R2 image signals and applies, for each pixel, a gain corresponding to the oxygen saturation level to these image signals. The image generation unit 76 uses the B2 image signals, the G2 image signals, and the R2 image signals to which gains are applied to generate RGB image data. For example, for a pixel for which the oxygen saturation level is 60% or higher, the image generation unit 76 multiplies each of the B2 image signal, the G2 image signal, and the R2 image signal by the same gain "1". On the other hand, for a pixel for which the oxygen saturation level is lower than 60%, the image generation unit 76 multiplies the B2 image signal by a gain smaller than "1" and multiplies the G2 image signal and the R2 image signal by a gain equal to or larger than "1". The B2 image signals, the G2 image signals, and the R2 image signals after this gain processing are used to generate RGB image data, which corresponds to the oxygen saturation image.

In the oxygen saturation image generated by the image generation unit 76, a high-oxygen region (a region in which the oxygen saturation levels are from 60 to 100%) is represented in colors the same as those of a normal observation image. On the other hand, a low-oxygen region in which the oxygen saturation levels are below a specific value (a region in which the oxygen saturation levels are from 0 to 60%) is represented in colors (pseudo colors) different from those of a normal observation image.

Note that, in this embodiment, the image generation unit 76 performs multiplication by gains for representation in pseudo colors only for a low-oxygen region; however, the image generation unit 76 may apply gains corresponding to oxygen saturation levels also for a high-oxygen region to represent the entire oxygen saturation image in pseudo colors. Further, the low-oxygen region and the high-oxygen region are determined on the basis of an oxygen saturation level of 60%; however, this boundary may be set to any value.

The frame adjustment unit 68 (see FIG. 4) changes the number of frames to be displayed per unit time for the normal image and/or oxygen saturation image to make various adjustments for frames. Accordingly, a problem that may occur due to an insufficient frame rate in a case where, for example, motion of a displayed photographic subject is large is alleviated. The frame adjustment unit 68 will be described in detail below.

The display control unit 56 determines the display method for a normal image and a computational image sent from the frame adjustment unit 68 on the basis of the computational processing time taken to generate the oxygen saturation image and the amount of relative motion of the photographic subject. As the display method based on the computational processing time, it is preferable to use a method in which display of the normal image is delayed by the computational processing time. Accordingly, a time lag between obtaining of the normal image and obtaining of the oxygen saturation image is eliminated, and an uneasy feeling felt in a case of viewing two types of displayed images, namely, the normal image and the oxygen saturation image, is relieved. The display control unit 56 will be described in detail below.

In this embodiment, the monitor 18 is a display unit. The monitor 18 displays a normal image and a computational image in accordance with the display method determined by the display control unit 56.

Figure 9:
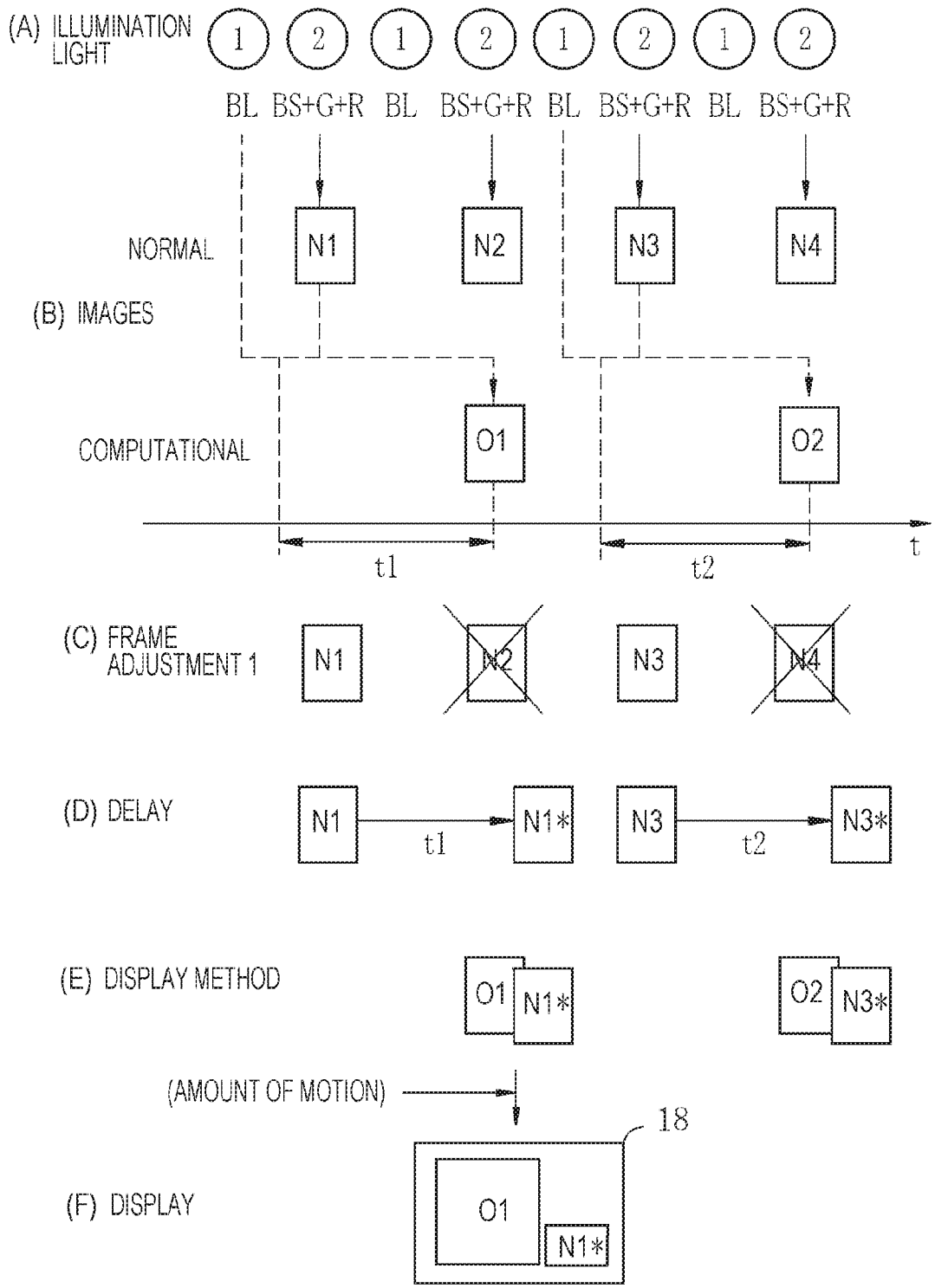
FIG. 9 includes diagrams for explaining adjustment 1 made by a frame adjustment unit and a delay process.

This embodiment is specifically described below with reference to the drawings. FIG. 9 illustrates radiation of illumination light (FIG. 9(A) Illumination Light), obtained images (FIG. 9(B) Images, Normal and Computational), frame adjustment (FIG. 9(C) Frame Adjustment 1), delays of normal images (FIG. 9(D) Delay), a display method determined by the display control unit 56 (FIG. 9(E) Display Method), and display on the monitor 18 (FIG. 9(F) Display) along a time axis t. FIG. 9 schematically illustrates images obtained in a certain period, passage of time, etc. First, regarding illumination light, switching between the first measurement light emission mode (FIG. 9(A) 1) in which the second blue light BL is emitted and the second measurement light emission mode (FIG. 9(A) 2) in which the first blue light BS, the green light G, and the red light R are simultaneously emitted is performed at specific intervals (FIG. 9(A) Illumination Light). These intervals are constant. An image obtained at the time of light emission in the second measurement light emission mode is input to the normal image generation unit 62 as a normal image. "N1", "N2", "N3", and "N4" represent normal images, and "N1" is obtained before the time when "N2" is obtained (FIG. 9(B) Normal). A first image obtained at the time of light emission in the first measurement light emission mode and a second image obtained at the time of light emission in the second measurement light emission mode are input to the computational image generation unit 64, and an oxygen saturation image is generated. "O1" and "O2" represent oxygen saturation images each generated on the basis of the image obtained at the time of light emission in the first measurement light emission mode and the image obtained at the time of light emission in the second measurement light emission mode (FIG. 9(B) Computational). "O1" is obtained before the time when "O2" is obtained.

Frame adjustment 1 made by the frame adjustment unit 68 is an adjustment for decreasing the number of frames to be displayed per unit time for the normal image. In frame adjustment 1 in FIG. 9(C) (hereinafter referred to as adjustment 1), normal images are changed so that the number of frames to be displayed per unit time is decreased and the frame rate is decreased to about one-half. In this embodiment, because of computation of oxygen saturation levels by the computational image generation unit 64, the frame rate of the oxygen saturation image becomes about half the frame rate of the normal image. Accordingly, in adjustment 1 made by the frame adjustment unit 68, the frame rate of the normal image is decreased to one-half (FIG. 9(C)). Note that the frame rate described herein means the number of frames to be displayed per unit time. Among the obtained normal images, "N1" and "N3" selected in adjustment 1 are used, these are provided for display, and "N2" and "N4" are not displayed. With the adjustment for decreasing the frame rate of the normal image, in adjustment 1, an adjustment is made so that the difference between the number of frames of normal images to be displayed per unit time and the number of frames of oxygen saturation images to be displayed per unit time becomes smaller, and these numbers become substantially the same. The overview of adjustment 1 is as described above. Methods for frame adjustment other than adjustment 1 will be described below.

The computational processing time detection unit 66 detects time t1 taken to generate the oxygen saturation image "O1" from the first image and the second image by computation of oxygen saturation levels. The display control unit 56 uses the computational processing time t1 to perform a process (hereinafter referred to as a delay process) for delaying the display time of "N1" that is obtained at the same time when the second image used for "O1" is obtained with the same illumination light by time t1 taken to generate the oxygen saturation image "O1" to make "N1*." In this embodiment, the computational processing time detection unit 66 measures the time taken to generate an oxygen saturation image each time the oxygen saturation image is generated. Therefore, the display control unit 56 performs a process for delaying the display time of "N3" by time t2 taken to generate the oxygen saturation image "O2" to make "N3*" (FIG. 9(D) Delay). Then, the display control unit 56 sets a display method for displaying the oxygen saturation image "O1" and "N1*" at substantially the same time (FIG. 9(E) Display Method). Note that regarding the frame adjustment and the delay process, the frame adjustment may be first made, and thereafter, the delay process may be performed as in this embodiment; however, the delay process may be first performed, and thereafter, the frame adjustment may be made, that is, the frame adjustment and the delay process may be performed in any order.

The display control unit 56A determines the display method for the normal image "N1*" for which display is delayed and the oxygen saturation image "O1" from a result obtained by the motion detection unit 50, and thereafter, converts the images to video signals for enabling full-color display on the monitor 18. The motion detection unit 50 is configured as described above and detects a result indicating whether the amount of relative motion of the photographic subject is smaller than the threshold value or equal to or larger than the threshold value. The amount of relative motion of the photographic subject described here can be obtained from the sum of motion vectors in time t1 taken to generate the oxygen saturation image. The threshold value can be set in advance or can be changed at that time. In the example illustrated in FIG. 9, the amount of motion in time t1 is smaller than the threshold value, and therefore, it is determined that the photographic subject is not moving and that the observation target is being observed in detail, and the display control unit 56 displays the oxygen saturation image "O1" in a large area as a main image and displays the normal image "N1*" for which display is delayed in a small area as a sub-image on one monitor, namely, the monitor 18, as illustrated in FIG. 9(F). Note that in FIG. 9(F), only one set, namely, the pair of the oxygen saturation image "O1" and the normal image "N1*", are displayed on the monitor 18; however, the other pairs of normal images and oxygen saturation images are successively displayed on the monitor 18 one after another in accordance with the same procedure. Therefore, after the pair of "O1" and "N1*" have been displayed, a pair of "O2" and "N3*" are displayed in accordance with the amount of motion in time t2. Note that when the display method is determined in accordance with the amount of motion, a display method that enables easier view can be set by adjusting the period for which the amount of motion is calculated, the calculation method, the threshold value, etc.

In addition to adjustment 1 described above, the frame adjustment unit 68 may make frame adjustment 2 to frame adjustment 4 described below.

(1) Frame Adjustment 2

Frame adjustment 2 (hereinafter referred to as adjustment 2) made by the frame adjustment unit 68 is an adjustment for increasing the number of frames to be displayed per unit time for the oxygen saturation image. In this embodiment, a computational image is an oxygen saturation image, and two images are used to generate one computational image. In adjustment 2, an adjustment is made in which generated one oxygen saturation image is replicated to make two oxygen saturation images.

Figure 10:
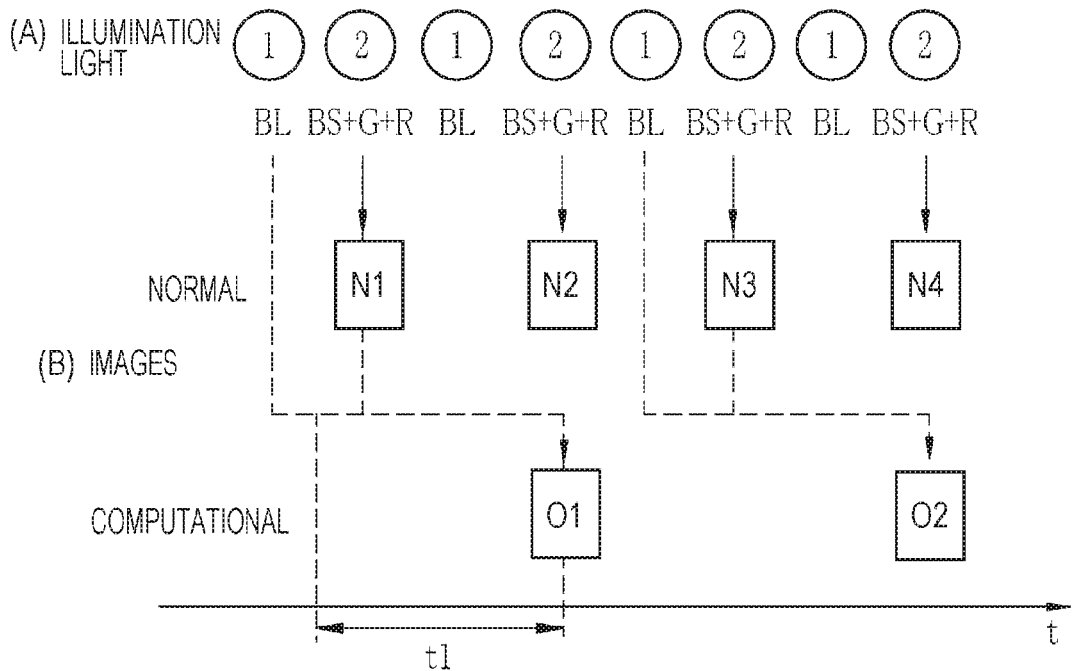
FIG. 10 includes diagrams for explaining adjustment 2 made by the frame adjustment unit and a delay process.
Figure 10:
Figure 10:
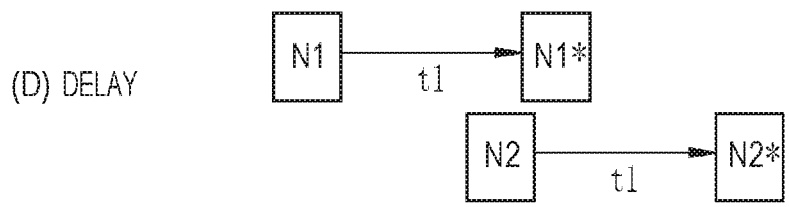
Figure 10:
Figure 10:

A specific example is illustrated in FIG. 10. FIG. 10 illustrates the relations among radiation of illumination light (FIG. 10(A) Illumination Light), obtained normal images "N1", "N2", "N3", and "N4" and oxygen saturation images "O1" and "O2" (FIG. 10(B) Images, Normal and Computational), adjustment 2 made by the frame adjustment unit 68 (FIG. 10(C) Frame Adjustment 2), delays of normal images (FIG. 10(D) Delay), a display method determined by the display control unit 56 (FIG. 10(E) Display Method), and display (FIG. 10(F) Display) along the time axis t. FIG. 10 schematically illustrates images obtained in a certain period, passage of time, etc. The illumination light is the same as that described with reference to FIG. 9. To generate one oxygen saturation image "O1", two images, namely, an image obtained in the first measurement light emission mode and an image obtained in the second measurement light emission mode, are used. In adjustment 2, a process for replicating the generated one oxygen saturation image "O1"

to display two oxygen saturation images "O1" is performed (FIG. 10(C)). Accordingly, the number of frames for the oxygen saturation image is increased and becomes equal to that of the normal images "N1" and "N2". The overview of adjustment 2 is as described above.

The computational processing time detection unit 66 detects time t1 taken to generate the oxygen saturation image "O1" from the first image and the second image by computation of oxygen saturation levels. The display control unit 56 uses the computational processing time t1 to perform a delay process for delaying the display time of "N1" that is obtained at the same time when the second image used for "O1" is obtained with the same illumination light by time t1 taken to generate the oxygen saturation image "O1" to make "N1*". For the display time of "N2", a delay process for delaying by time t1 described above is performed to make "N2*". In this embodiment, the computational processing time detection unit 66 measures the time taken to generate an oxygen saturation image each time the oxygen saturation image is generated. Therefore, the display control unit 56 performs a process for delaying the display time of "N1" and that of "N2" by time t1 taken to generate the oxygen saturation image "O1" to make "N1*" and "N2*" (FIG. 10(D) Delay).

Next, the display control unit 56 changes the display method on the basis of a result obtained by the motion detection unit 50 and converts the normal image and the oxygen saturation image from the frame adjustment unit 68 to video signals for enabling full-color display on the monitor 18. The motion detection unit 50 is configured as described above, and detects and sends to the display control unit 56 a result indicating whether the amount of relative motion of the photographic subject is smaller than the threshold value or equal to or larger than the threshold value. In the example illustrated in FIG. 10, the amount of motion is equal to larger than the threshold value, and therefore, the display control unit 56 uses a method for displaying the normal image in a large display area and the oxygen saturation image in a small display area as illustrated in FIG. 10(F), and the images are displayed on the monitor 18. Note that in FIG. 10(F), only one set, namely, the pair of the normal image "N1*" and the oxygen saturation image "O1", are displayed on the monitor 18; however, the other pairs of normal images and oxygen saturation images are successively displayed on the monitor 18 one after another in accordance with the same procedure. Therefore, after the pair of "N1*" and "O1*" have been displayed, a pair of "N2*" and "O1" are displayed in accordance with the amount of motion in time t1.

For example, in a case where the frame rate becomes one-half due to computational processing for generating an oxygen saturation image, with adjustment 2, the frame rate of the normal image and that of the oxygen saturation image become substantially the same, and the frame rate of the normal image is not decreased. Therefore, a problem caused by a decrease in the frame rate of the normal image, namely, for example, a problem of non-smooth image motion and difficulty in grasping the position of the endoscope specifically in a case where the relative motion of the photographic subject is large, is less likely to occur. Further, in a case where motion is large, the normal image is displayed in a large display area, which makes it easier to swiftly grasp the position of the endoscope.

(2) Frame Adjustment 3

Frame adjustment 3 (hereinafter referred to as adjustment 3) made by the frame adjustment unit 68 is an adjustment for generating an interpolation frame for a computational image on the basis of a relative motion vector of the photographic subject detected by the motion detection unit 50 from a normal image. In this embodiment, the motion detection unit 50 detects the spatial distance between certain pixels in two frames and the direction thereof as a motion vector as described above. Such motion vectors in a plurality of frames in a specific period are added up so that the relative motion vector of the photographic subject in the specific period can be detected. In a case where the amount of motion obtained from this motion vector is equal to or larger than the threshold value, it is determined that motion of the photographic subject is large, and an interpolation frame for an oxygen saturation image is created. The interpolation frame is an image created by performing for a specific oxygen saturation image a interpolation process for creating an image in which the photographic subject is moved by the above-described motion vector. On the other hand, in a case where the amount of motion obtained from the motion vector is smaller than the threshold value, it is determined that motion of the photographic subject is small, and an interpolation frame for an oxygen saturation image is not created. The threshold value and the number of interpolation frames to be created, that is, a relationship between the amount of motion and the number of interpolation frames to be created in the interpolation process, can be set in advance or can be changed at that time.

Figure 11:
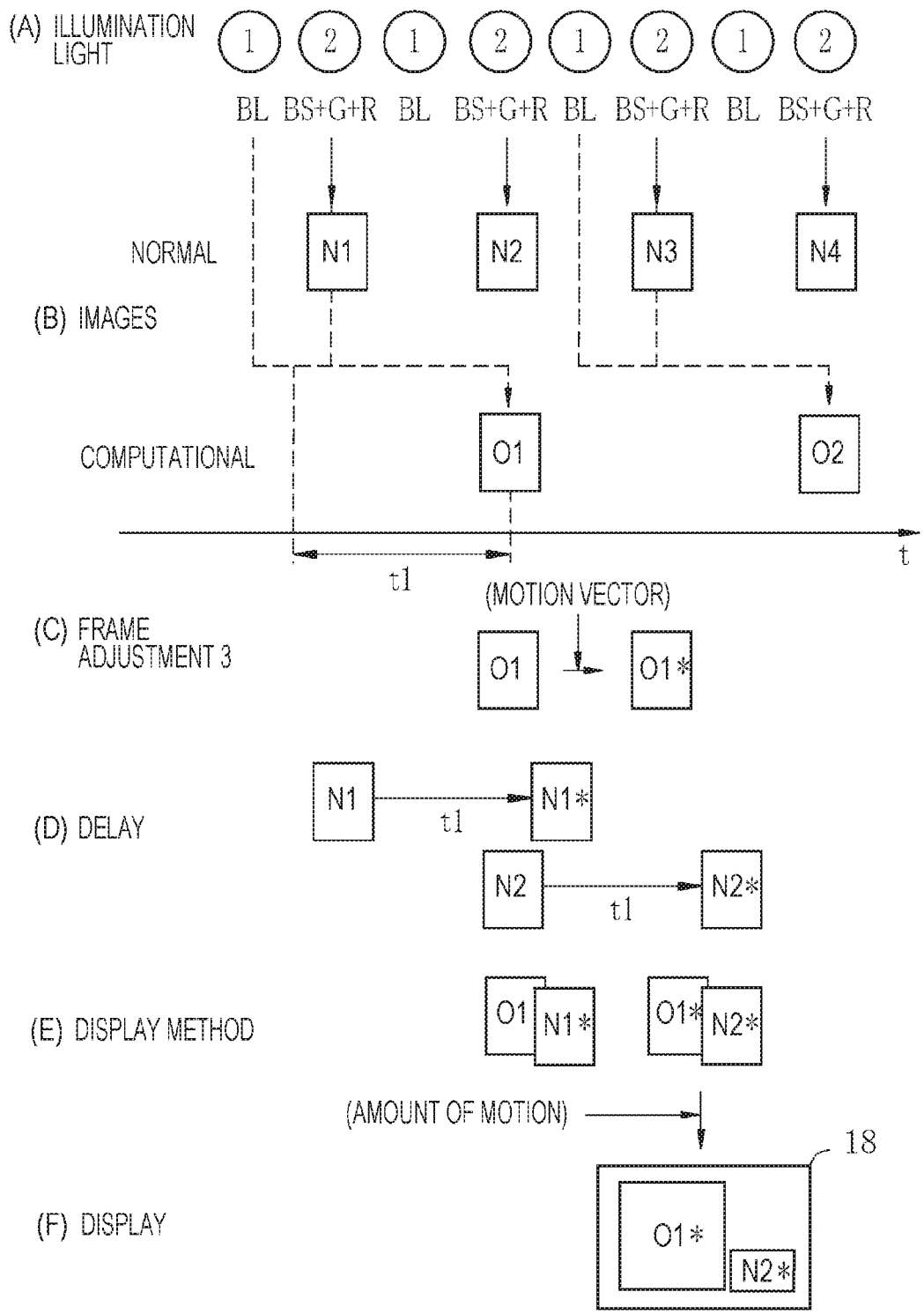
FIG. 11 includes diagrams for explaining adjustment 3 made by the frame adjustment unit and a delay process.

A specific example is illustrated in FIG. 11. FIG. 11 illustrates the relations among radiation of illumination light (FIG. 11(A) Illumination Light), obtained normal images "N1", "N2", "N3", and "N4" and oxygen saturation images "O1" and "O2" (FIG. 11(B) Images, Normal and Computational), adjustment 3 made by the frame adjustment unit 68 (FIG. 11(C) Frame Adjustment 3), delays of normal images (FIG. 11(D) Delay), a display method determined by the display control unit 56 (FIG. 11(E) Display Method), and display (FIG. 11(F) Display) along the time axis t. FIG. 11 schematically illustrates images obtained in a certain period, passage of time, etc. The illumination light is the same as that described with reference to FIG. 9. To generate one oxygen saturation image "O1", two images, namely, an image obtained in the first measurement light emission mode and an image obtained in the second measurement light emission mode, are used. In adjustment 3, a process for generating an interpolation frame "O1*" from the generated one oxygen saturation image "O1" on the basis of the motion vector in time t1 to display two oxygen saturation images "O1" and "O1*" is performed (FIG. 11(C)). The overview of adjustment 3 is as described above.

Next, the display control unit 56 changes the display method on the basis of a result obtained by the motion detection unit 50 and converts the normal image and the oxygen saturation image from the frame adjustment unit 68 to a video that can be displayed on the monitor 18 in full color. A delay process performed by the computational processing time detection unit 66 (FIG. 11(D)), determination of the display method by the display control unit 56 (FIG. 11(E)), and display on the monitor 18 (FIG. 11(F)) are the same as those described in (1) Frame Adjustment 2 above. Note that the case where the amount of motion is smaller than the threshold value is illustrated here, and the display control unit 56 uses the method for displaying the oxygen saturation image in a large display area and the normal image in a small display area, and the images are displayed on the monitor 18 as illustrated in FIG. 11(F).

With adjustment 3, the number of frames of the oxygen saturation images "O1" and "O1*" are equal to the number of frames of the normal images "N1" and "N2", and the images "O1" and "O1*" become images that represent different positions in accordance with the motion of the photographic subject. Therefore, specifically in the case where motion of the photographic subject is large, a problem caused by a decrease in the frame rate of the normal image is less likely to occur, and a problem caused by a decrease in the frame rate of the oxygen saturation image is also less likely to occur. Accordingly, motion in the oxygen saturation image as well as in the normal image becomes smooth, and both images are displayed without giving an uneasy feeling.

(3) Frame Adjustment 4

Frame adjustment 4 (hereinafter referred to as adjustment 4) made by the frame adjustment unit 68 is an adjustment for instructing the computational image generation unit 64 to use, in computational processing at least twice or more, one of the images that are required for generating an oxygen saturation image to generate at least two computational images. For example, in this embodiment, a computational image is an oxygen saturation image, and one of each of the two types of images is used to generate one computational image. Therefore, an image of one type is normally used once. In adjustment 4, an image of one type is used with an image of the other type obtained before or after the image of one type is obtained to generate a computational image. Accordingly, the time taken to generate a computational image is reduced, and an uneasy feeling felt about a difference in the obtaining time in a case of comparing a normal image and a computational image can be relieved.

Figure 12:
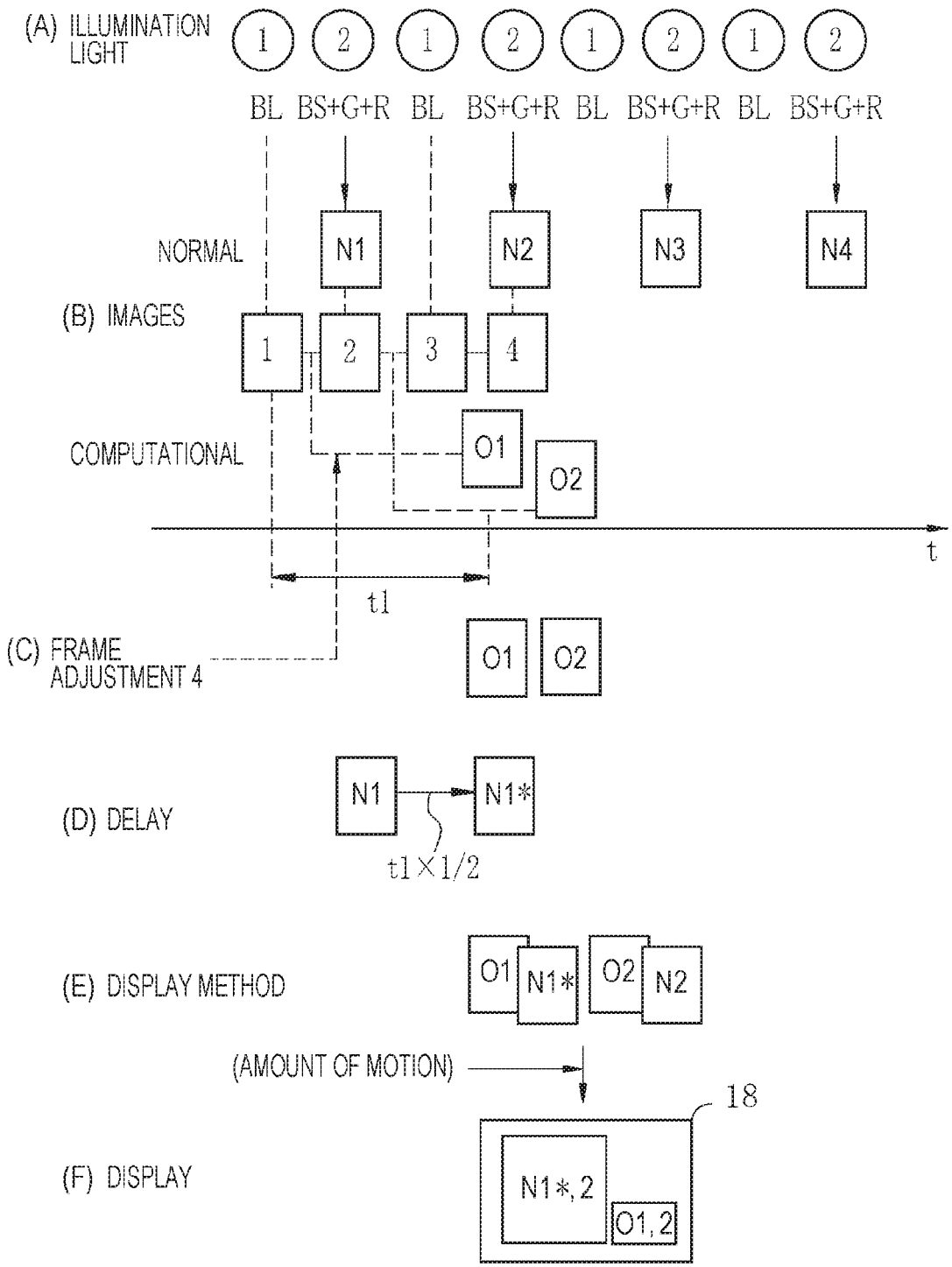
FIG. 12 includes diagrams for explaining adjustment 4 made by the frame adjustment unit and a delay process.

A specific example is illustrated in FIG. 12. FIG. 12 includes diagrams for explaining the relations among radiation of illumination light (FIG. 12(A) Illumination Light), obtained normal images and oxygen saturation images (FIG. 12(B) Images, Normal and Computational), adjustment 4 made by the frame adjustment unit 68 (FIG. 12(C) Frame Adjustment 4), a delay of a normal image (FIG. 12(D) Delay), a display method (FIG. 12(E) Display Method), and display (FIG. 12(F) Display) along the time axis t. The illumination light is the same as that described with reference to FIG. 9. The normal images are images obtained at the time of light emission in the second measurement light emission mode and input to the normal image generation unit 62. The image "1" is an image "1" obtained at the time of light emission in the first measurement light emission mode and input to the computational image generation unit 64 to calculate oxygen saturation levels (see FIG. 4) in this embodiment. To generate one oxygen saturation image "O1", two images "1" and "2" are used. To generate the next oxygen saturation image "O2", "2" and "3" are used as two images instead of "3" and "4". These oxygen saturation images thus adjusted by the frame adjustment unit 68 are sent to the display control unit 56 (see FIG. 2). The overview of adjustment 4 is as described above.

The computational processing time detection unit 66 detects time t1 taken to generate the oxygen saturation image "O1" from the first image and the second image by computation of oxygen saturation levels. The display control unit 56 uses the computational processing time t1 to perform a delay process for delaying the display time of "N1" that is obtained at the same time when the second image used for "O1" is obtained with the same illumination light by half the time t1 (t1×½) taken to generate the oxygen saturation image "O1" to make "N1*". The display control unit 56 determines that the obtaining time of "N2" and that of "O2" are close to each other, and does not perform a delay process (FIG. 12(D) Delay).

Next, the display control unit 56 changes the display method on the basis of a result obtained by the motion detection unit 50 and converts the normal image and the oxygen saturation image from the frame adjustment unit 68 to a video that can be displayed on the monitor 18 in full color. The motion detection unit 50 is configured as described above, and detects and sends to the display control unit 56 a result indicating whether the amount of relative motion of the photographic subject is smaller than the threshold value or equal to or larger than the threshold value. In the example illustrated in FIG. 12, the amount of motion is equal to larger than the threshold value, and therefore, the display control unit 56 uses the method for displaying the normal image as a large-size image and the oxygen saturation image as a small-size image as illustrated in FIG. 12F, and the images are displayed on the monitor 18. FIG. 12(F) illustrates a normal image "N1*,2" representing that "N1*" and "N2" are successively displayed on the monitor 18. Similarly, FIG. 12(F) illustrates an oxygen saturation image "O1,2" representing that "O1" and "O2" are successively displayed on the monitor 18. In accordance with the same procedure, the other pairs of normal images and oxygen saturation images are successively displayed on the monitor 18 one after another.

With adjustment 4 made by the frame adjustment unit 68 and determination of the display method by the display control unit 56, an uneasy feeling felt about display resulting from a difference in the frame rate between the normal image and the computational image is eliminated, and the display method is automatically changed. Therefore, the user can easily grasp the endoscope observation position, and the computational image becomes easier to view.

Figure 13:
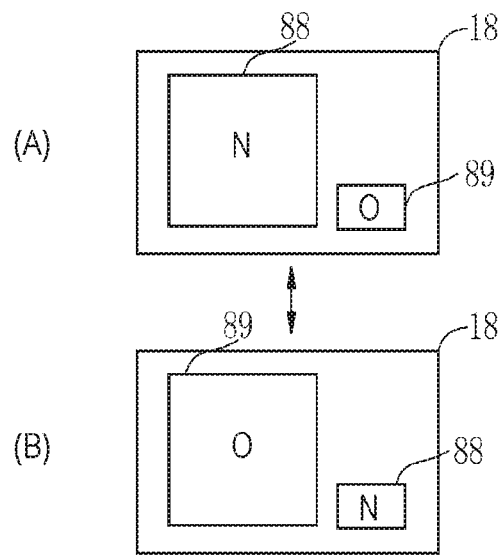
FIG. 13 includes diagrams for explaining a method for displaying a normal image and a computational image on a monitor.

As the display method for a normal image and an oxygen saturation image, the following methods can be preferably used. As illustrated in FIG. 13(A), in a case of, for example, displaying both a normal image 88 and an oxygen saturation image 89 on one monitor, in a case where the amount of motion is equal to or larger than the threshold value, the display control unit 56 uses the display method for displaying the normal image 88 as an image larger in size than the oxygen saturation image 89 and the oxygen saturation image 89 as an image smaller in size than the normal image 88. In the case where the amount of motion is equal to or larger than the threshold value, it is considered that, for example, attention is not paid on a lesion and the endoscope is moving, and the display method with which the position of the endoscope can be more easily grasped and the endoscope can be more safely moved is used.

On the other hand, in a case where the amount of motion is smaller than the threshold value, as illustrated in FIG. 13(B), the display method for displaying the oxygen saturation image 89 as a large-size image and the normal image 88 as an image smaller in size than the oxygen saturation image 89 is used. In the case where the amount of motion is smaller than the threshold value, it is considered that, for example, attention is paid on a lesion present in a part of the photographic subject, and the display method with which the oxygen saturation level can be grasped at a glance is used. In this case, it is less likely to move the endoscope to a large extent, and therefore, even when the normal image 88 with which the position of the endoscope can be easily grasped is displayed as an image smaller in size than the oxygen saturation image 89, no problem occurs in most cases.

Note that display of the normal image 88 and the oxygen saturation image 89 as images having different sizes as illustrated in FIG. 13(A) and FIG. 13(B) is automatically switched in accordance with the relative motion of the photographic subject, namely, for example, the motion of the endoscope, as the amount of motion is detected in real time by the motion detection unit 50. Note that, for example, the frequency of switching can be adjusted as desired by presetting. Further, as the normal image 88 displayed on the monitor, a normal image at a position different from the actual position of the endoscope may be displayed in a case where, for example, the frame rate is decreased with adjustment 1. However, the original frame rate is sufficiently high, and therefore, a problem is less likely to occur in an endoscope operation even if the frame rate is decreased to one-half. The difference between the actual position and the position of display is eliminated when, for example, the amount of motion is smaller than the threshold value, and therefore, there is little problem. Further, for example, it is possible to end the multi-observation mode and switch to the normal mode. Also by such a user operation, the difference can be eliminated.

Figure 14:
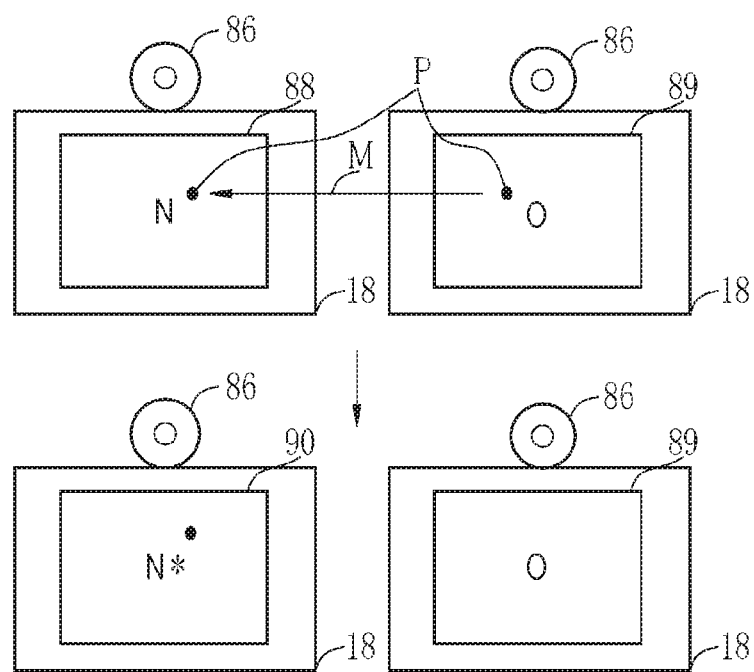
FIG. 14 is a diagram for explaining a method for displaying a normal image and a computational image on the monitor.

As another display method for a normal image and an oxygen saturation image, also the following method is preferable. For example, in a case where a normal image and an oxygen saturation image are each displayed on a corresponding one of the monitors and the normal image and the oxygen saturation image are compared with each other on the two monitors, the display method is changed on the basis of a result obtained by the motion detection unit 50 as illustrated in FIG. 14. In FIG. 14, the normal image 88 is displayed on the left-side monitor and the oxygen saturation image 89 is displayed on the right-side monitor. Each monitor 18 is provided with a camera 86, which is part of a line-of-sight detection device (part of the line-of-sight detection device is not illustrated). The line-of-sight detection device can recognize the eye of a person and the point of gaze P with the camera 86, and therefore, can detect which of the right-side and left-side monitors 18 the user is viewing. Further, the line-of-sight detection device includes a line-of-sight movement detection unit (not illustrated) and can detect a line-of-sight movement time taken for specific movement of the point of gaze P, for example, movement of the point of gaze P from the point of gaze P on the right-side monitor to the point of gaze P on the left-side monitor (represented by M in FIG. 14).

Figure 15:
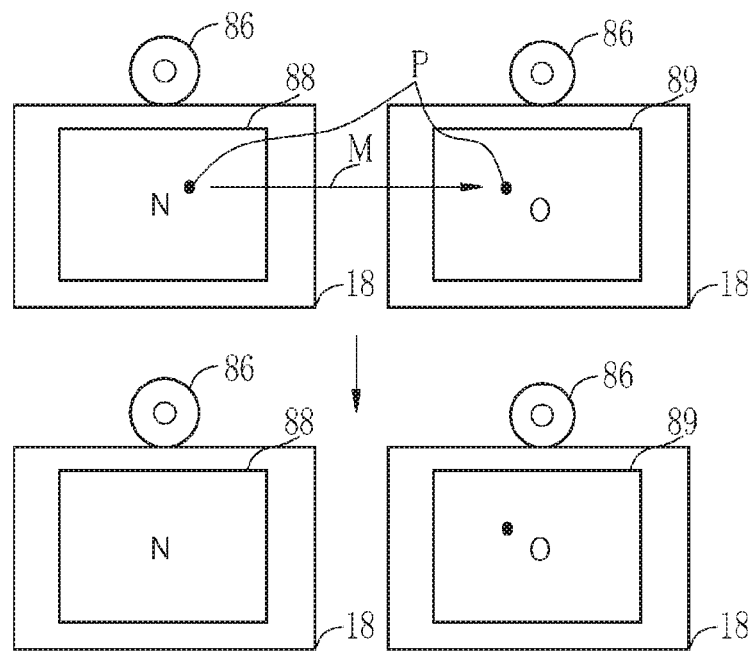
FIG. 15 is a diagram for explaining a method for displaying a normal image and a computational image on the monitor.

As illustrated in FIG. 14, in a case where the point of gaze P of the user moves (M) from the monitor 18 that displays the oxygen saturation image 89 to the monitor 18 that displays the normal image 88, the user may feel that the normal image 88 that the user is viewing after the movement (M) is the normal image 88 at a time point ahead by time t3 taken for the movement (M). Specifically, in a case where the amount of motion of the photographic subject is equal to or larger than the threshold value, the user may feel that the normal image 88 that the user is viewing after the movement is the normal image 88 at a time point further ahead. Therefore, in this case, the normal image subjected to a delay process is displayed. The delay process is the same as that described above. In a case of displaying the normal image, a delay process for delaying by time t3 is performed. In FIG. 14, a normal image 90 subjected to the delay process is represented by "N*". On the other hand, as illustrated in FIG. 15, in a case where the point of gaze P of the user moves (M) from the monitor 18 that displays the normal image 88 to the monitor 18 that displays the oxygen saturation image 89, the user is less likely to feel that the oxygen saturation image 89 is an image at a time point ahead as described above, and therefore, the delay process is not performed.

Figure 16:
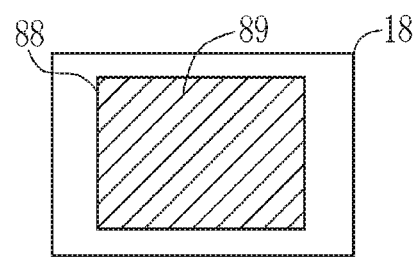
FIG. 16 is a diagram for explaining a method for displaying a normal image and a computational image on the monitor.

As yet another display method for a normal image and an oxygen saturation image, also the following method is preferable. As illustrated in FIG. 16, the display control unit 56 can use a display method in which the frame adjustment unit 68 makes any of the above-described adjustment 1 to adjustment 4 or a combination thereof, and thereafter, the oxygen saturation image 89 is overlaid on the normal image 88 and displayed on the monitor. In FIG. 16, the oxygen saturation image 89 is illustrated as a shaded image. With this display method, the computational image is displayed so as to be less noticeable in a case where the amount of motion is equal to or larger than the threshold value, and the computational image is displayed so as to be noticeable in a case where the amount of motion is smaller than the threshold value. Specifically, in the case where the amount of motion is equal to or larger than the threshold value, the lightness of the color of the overlaid computational image is increased so as to be less noticeable. On the other hand, in the case where the amount of motion is smaller than the threshold value, the lightness of the color of the computational image is decreased so as to be more noticeable. Note that in the above, the normal image 88 and the oxygen saturation image 89 may be images subjected to frame adjustment or may be images not subjected to frame adjustment.

As described above, in the endoscope system 10, the frame adjustment unit 68 makes a frame adjustment on the basis of the computational processing time detected by the computational processing time detection unit 66 and the amount of motion detected by the motion detection unit 50, and the display control unit 56 determines the display method. Accordingly, display can be performed while an uneasy feeling resulting from a delay of the computational image and motion of the photographic subject is relieved. Consequently, the endoscope system is a system with which the observation position is easily grasped while a normal image and a computational image are simultaneously displayed.

Second Embodiment

In a second embodiment, instead of the LEDs 20a to 20e of five colors described in the first embodiment above, a broadband light source, such as a xenon lamp, and a rotating filter are used to illuminate an observation target. Further, instead of the image sensor 36, which is a color image sensor, a monochrome image sensor is used to capture images of an observation target. As the observation modes, three types, namely, the normal mode, the oxygen saturation mode, and the multi-observation mode, are provided. In the multi-observation mode, switching between the normal mode and the oxygen saturation mode is automatically performed. A description of only part different from that in the first embodiment is mainly given below, and a description of part the same as that in the first embodiment is omitted.

Figure 17:
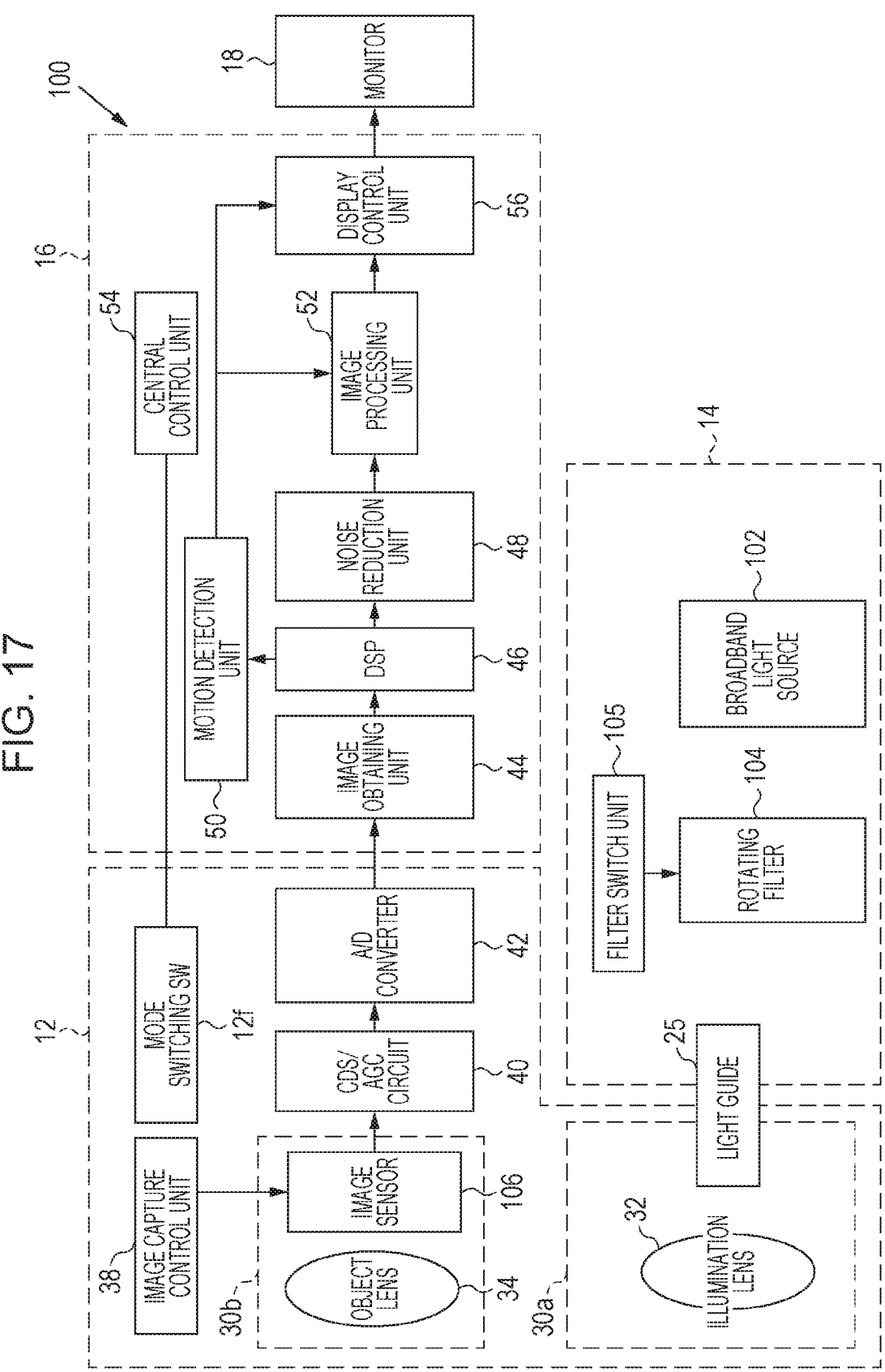
FIG. 17 is a block diagram illustrating functions of an endoscope system according to a second embodiment.

As illustrated in FIG. 17, in an endoscope system 100 according to the second embodiment, the light source device 14 is provided with a broadband light source 102, a rotating filter 104, and a filter switch unit 105 instead of the LEDs 20a to 20e of five colors. Further, the image capture optical system 30b is provided with a monochrome image sensor 106, in which color filters are not provided, instead of the image sensor 36, which is a color image sensor.

The broadband light source 102 is, for example, a xenon lamp or a white LED and emits white light in a wavelength range extending from blue to red. The rotating filter 104 includes an inner filter 108 provided closer to the center and an outer filter 109 provided further from the center (see FIG. 18). The filter switch unit 105 is a unit for moving the rotating filter 104 in the radial direction. When the normal mode is set by the mode switching SW 12f, the inner filter 108 of the rotating filter 104 is inserted in the optical path of white light. When the oxygen saturation mode is set, the outer filter 109 of the rotating filter 104 is inserted in the optical path of white light. When the multi-observation mode is set, the outer filter 109 of the rotating filter 104 is inserted in the optical path of white light.

Figure 18:
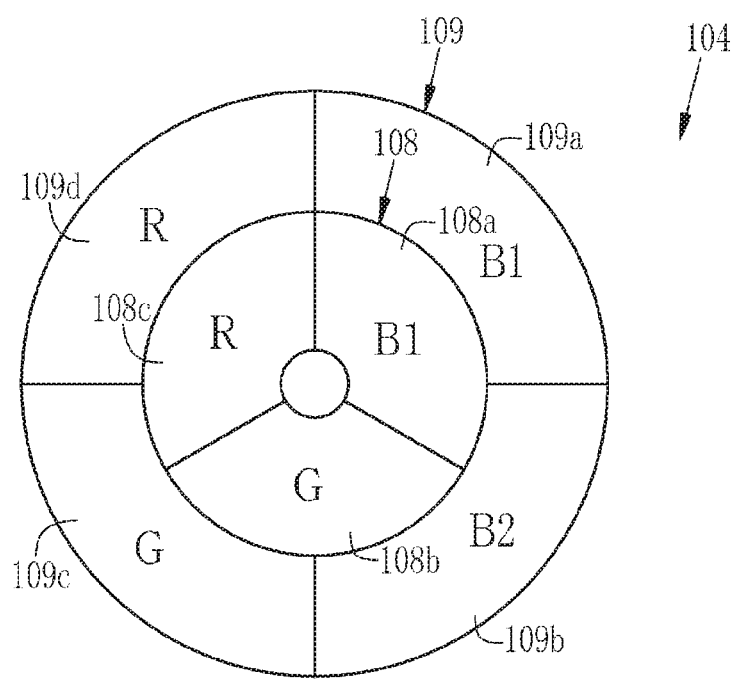
FIG. 18 is a plan view of a rotating filter.

As illustrated in FIG. 18, the inner filter 108 is provided with a B1 filter 108a that allows the first blue light BS in white light to pass therethrough, a G filter 108b that allows the green light G in the white light to pass therethrough, and an R filter 108c that allows the red light R in the white light to pass therethrough, in the circumferential direction. Therefore, in the normal mode, the rotating filter 104 rotates so that the first blue light BS, the green light G, and the red light R are cyclically radiated onto an observation target.

The outer filter 109 is provided with a B1 filter 109a that allows the first blue light BS in white light to pass therethrough, a B2 filter 109b that allows the second blue light BL in the white light to pass therethrough, a G filter 109c that allows the green light G in the white light to pass therethrough, and an R filter 109d that allows the red light R in the white light to pass therethrough, in the circumferential direction. Therefore, in the oxygen saturation mode, the rotating filter 104 rotates so that the first blue light BS, the second blue light BL, the green light G, and the red light R are cyclically radiated onto an observation target. Further, in the multi-observation mode, the rotating filter 104 rotates so that the first blue light BS, the second blue light BL, the green light G, and the red light R are cyclically radiated onto an observation target.

In the endoscope system 100, in the normal mode, each time an observation target is illuminated with the first blue light BS, the green light G, or the red light R, image capturing of the observation target is performed with the monochrome image sensor 106. Accordingly, Bc image signals, Gc image signals, and Rc image signals are obtained. On the basis of these image signals of three colors, a normal image is generated.

On the other hand, in the oxygen saturation mode, each time an observation target is illuminated with the first blue light BS, the second blue light BL, the green light G, or the red light R, image capturing of the observation target is performed with the monochrome image sensor 106. Accordingly, B2 image signals, B1 image signals, G2 image signals, and R2 image signals are obtained. On the basis of these image signals of four colors, an oxygen saturation image is generated. Further, in the multi-observation mode, each time an observation target is illuminated with the first blue light BS, the second blue light BL, the green light G, or the red light R, image capturing of the observation target is performed with the monochrome image sensor 106. Accordingly, B2 image signals, B1 image signals, G2 image signals, and R2 image signals are obtained. On the basis of these image signals of four colors, an oxygen saturation image is generated with a method the same as that in the first embodiment. Further, on the basis of the B2 image signals, the G2 image signals, and the R2 image signals among the image signals, a normal image is generated with a method the same as that in the first embodiment.

Third Embodiment

In a third embodiment, instead of the LEDs 20a to 20e of five colors described in the first embodiment above, a laser light source and a fluorescent body are used to illuminate an observation target. As the observation modes, three types, namely, the normal mode, the oxygen saturation mode, and the multi-observation mode, are provided. In the multi-observation mode, switching between the normal mode and the oxygen saturation mode is automatically performed. A description of only part different from that in the first embodiment is mainly given below, and a description of part the same as that in the first embodiment is omitted.

Figure 19:
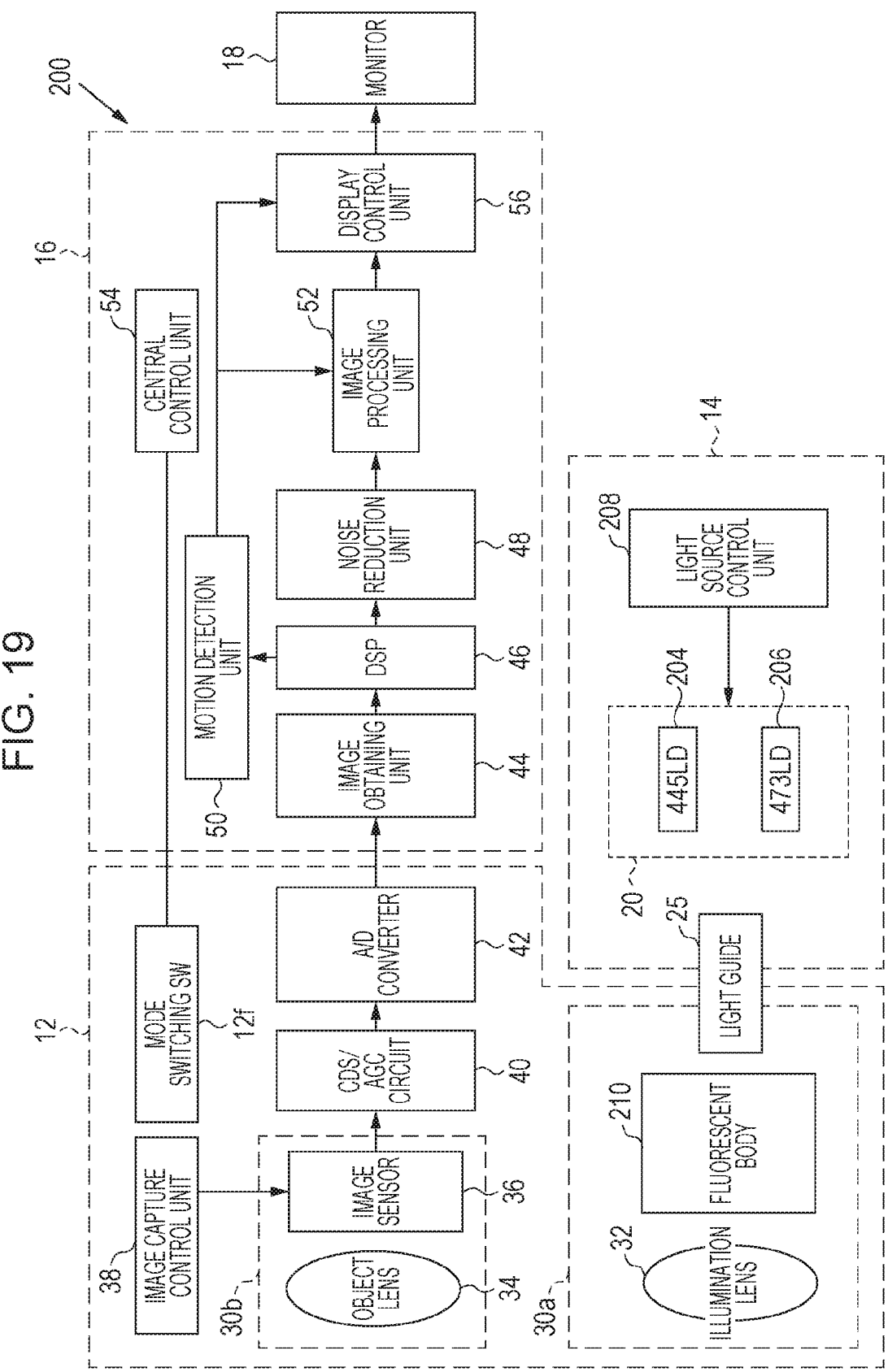
FIG. 19 is a block diagram illustrating functions of an endoscope system according to a third embodiment.

As illustrated in FIG. 19, in an endoscope system 200 according to the third embodiment, the light source 20 of the light source device 14 is provided with a blue laser light source (represented by "445LD" where LD represents "Laser Diode") 204 that emits blue laser light having a center wavelength of 445±10 nm and a blue-green laser light source (represented by "473LD") 206 that emits blue-green laser light having a center wavelength of 473±10 nm instead of the LEDs 20a to 20e of five colors. Light emission from a semiconductor light emitting element of each of the light sources 204 and 206 is individually controlled by a light source control unit 208.

In the normal mode, the light source control unit 208 turns on the blue laser light source 204. On the other hand, in the oxygen saturation mode, the light source control unit 208 turns on the blue laser light source 204 and the blue-green laser light source 206 alternately. In the multi-observation mode, an operation the same as that in the oxygen saturation mode is performed.

Note that it is preferable to set the half-width of the blue laser light or the blue-green laser light to about ±10 nm. Further, as the blue laser light source 204 and the blue-green laser light source 206, a broad-area InGaN laser diode can be used, and also an InGaNAs laser diode or a GaNAs laser diode can be used. Further, the above-described light sources may have a configuration in which a light emitting body, such as a light emitting diode, is used.

The illumination optical system 30a is provided with a fluorescent body 210 in addition to the illumination lens 32, and blue laser light or blue-green laser light from the light guide 25 enters the fluorescent body 210. The fluorescent body 210 is excited by the blue laser light to emit fluorescent light. Further, part of the blue laser light passes through the fluorescent body 210 without exciting the fluorescent body 210. Light that exits from the fluorescent body 210 passes through the illumination lens 32 to illuminate the interior of the body that is an observation target.

Figure 20:
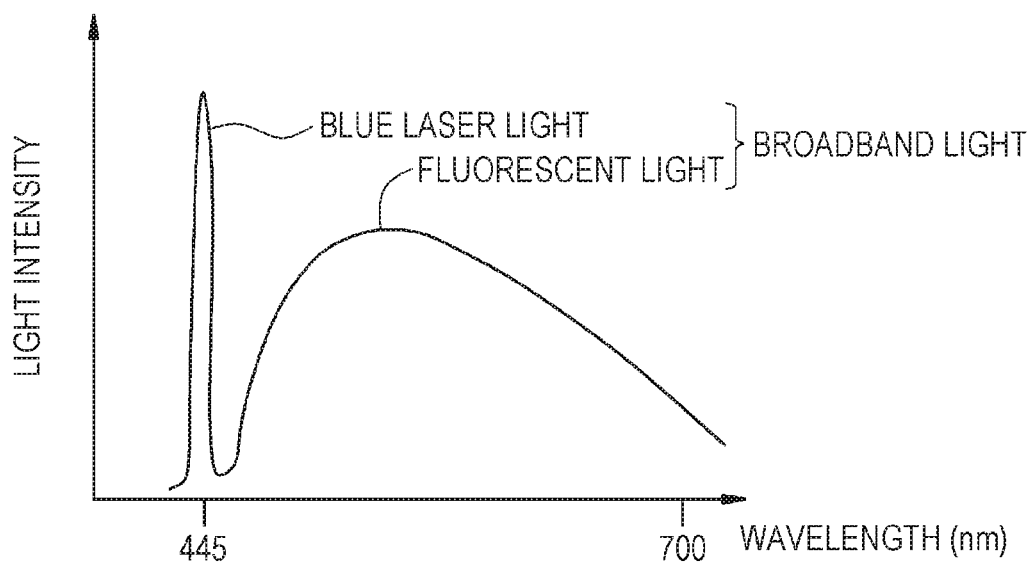
FIG. 20 is a graph illustrating the spectrum of broadband light.

Here, in the normal mode, the blue laser light mainly enters the fluorescent body 210, and therefore, an observation target is illuminated with broadband light as illustrated in FIG. 20, in which the blue laser light and fluorescent light emitted from the fluorescent body 210 excited by the blue laser light are multiplexed, as normal light. When image capturing of the observation target illuminated with the normal light is performed with the image sensor 36, a normal image formed of Bc image signals, Gc image signals, and Rc image signals is obtained.

Figure 21:
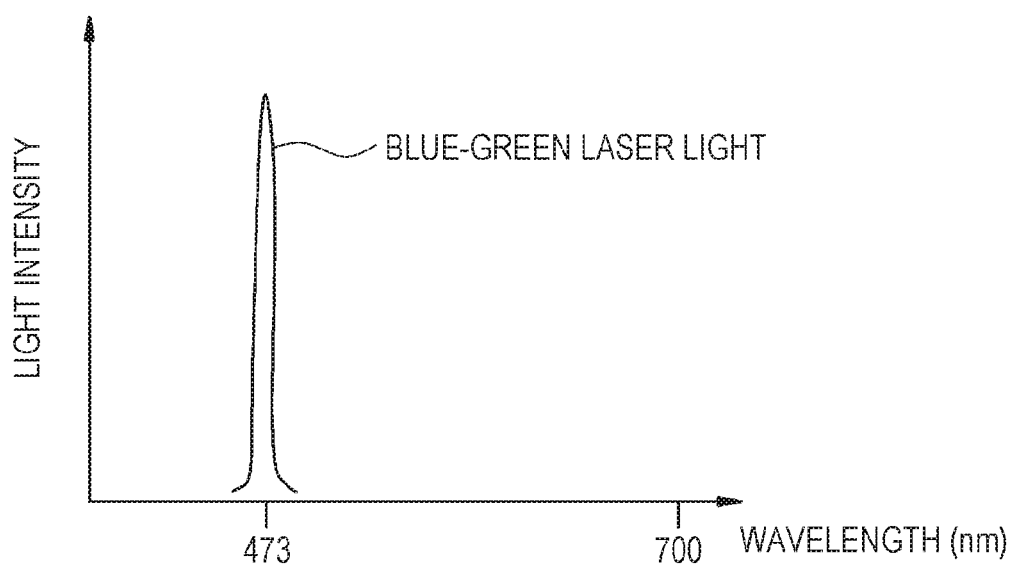
FIG. 21 is a graph illustrating the spectrum of blue-green laser light.

On the other hand, in the oxygen saturation mode and the multi-observation mode, when the blue laser light enters the fluorescent body 210, an observation target is illuminated with the broadband light illustrated in FIG. 20. When the blue-green laser light enters the fluorescent body 210, most of the blue-green laser light is not absorbed into the fluorescent body 210, and therefore, an observation target is illuminated with the blue-green laser light substantially directly, as illustrated in FIG. 21.

In the multi-observation mode, a signal output from each B pixel of the image sensor 36 during illumination with the blue-green laser light corresponds to the B1 image signal of the first embodiment described above. Further, a signal output form each B pixel of the image sensor 36 during illumination with the broadband light corresponds to the B2 image signal of the first embodiment described above, a signal output from each G pixel thereof corresponds to the G2 image signal of the first embodiment described above, and a signal output from each R pixel thereof corresponds to the R2 image signal of the first embodiment described above. On the basis of the B1 image signals, the B2 image signals, the G2 image signals, and the R2 image signals, the oxygen saturation levels are calculated. Further, on the basis of the B2 image signals, the G2 image signals, and the R2 image signals, a normal image is generated.

In the oxygen saturation mode, a signal output from each B pixel of the image sensor 36 during illumination with the blue-green laser light corresponds to the B1 image signal of the first embodiment described above. Further, a signal output from each B pixel of the image sensor 36 during illumination with the broadband light corresponds to the B2 image signal of the first embodiment described above, a signal output from each G pixel thereof corresponds to the G2 image signal of the first embodiment described above, and a signal output from each R pixel thereof corresponds to the R2 image signal of the first embodiment described above. On the basis of the B1 image signals, the B2 image signals, the G2 image signals, and the R2 image signals, the oxygen saturation levels are calculated.

Note that, as the fluorescent body 210, it is preferable to use a fluorescent body formed by including a plurality of types of fluorescent bodies (for example, fluorescent bodies such as a YKG fluorescent body or a BAM (BaMgAl$_{10}$O$_{17}$) fluorescent body) that absorb part of the blue laser light and are excited to emit green to yellow light. When a semiconductor light emitting element is used as an excitation light source of the fluorescent body 210 as in this example configuration, white light having high intensity can be obtained with a high light emission efficiency, the intensity of the white light can be easily adjusted, and changes in the color temperature and chromaticity of the white light can be made smaller.

In the above-described embodiments, the hardware configuration of the processing units, such as the image obtaining unit 44, the DSP 46, the noise reduction unit 48, the motion detection unit 50, the image processing unit 52, the central control unit 54, and the display control unit 56, included in the processor device 16 is implemented as various processors as described below. The various processors include a CPU (central processing unit), which is a general-purpose processor executing software (program) to function as various processing units, a programmable logic device (PLD), such as an FPGA (field-programmable gate array), which is a processor having a circuit configuration that is changeable after manufacture, and a dedicated electric circuit, such as a GPU (graphical processing unit), which is a processor having a circuit configuration specifically designed to perform various processes.

One processing unit may be configured as one of the various processors or a combination of two or more processors of the same type or different types (for example, a plurality of FPGAs, a combination of a CPU and an FPGA, or a combination of a CPU and a GPU). Further, a plurality of processing units may be configured as one processor. As the first example of configuring a plurality of processing units as one processor, a form is possible where one or more CPUs and software are combined to configure one processor, and the processor functions as the plurality of processing units, a representative example of which is a computer, such as a client or a server. As the second example thereof, a form is possible where a processor in which the functions of the entire system including the plurality of processing units are implemented as one IC (integrated circuit) chip is used, a representative example of which is a system on chip (SoC). As described above, regarding the hardware configuration, the various processing units are configured by using one or more of the various processors described above.

Further, the hardware configuration of the various processors is more specifically an electric circuit (circuitry) in which circuit elements, such as semiconductor elements, are combined.

Note that the present invention is applicable to a processor device built in a capsule-type endoscope system or to various medical image processing apparatuses in addition to the processor device built in the endoscope system as described in the above embodiments.

REFERENCE SIGNS LIST

10, 100, 200 endoscope system
12 endoscope
12*a* insertion part
12*b* operation part
12*c* bending part
12*d* distal end part
12*e* angle knob
12*f* mode switching SW
14 light source device
16 processor device
18 monitor
19 console
20 light source
20*a* V-LED
20*b* BS-LED
20*c* BL-LED
20*d* G-LED
20*e* R-LED
21, 208 light source control unit
23 optical path coupling unit
25 light guide
30*a* illumination optical system
30*b* image capture optical system
32 illumination lens
34 object lens
36, 106 image sensor
38 image capture control unit
40 CDS/AGC circuit
42 A/D converter
44 image obtaining unit
46 DSP
48 noise reduction unit
50 motion detection unit
52 image processing unit
54 central control unit
56 display control unit
58 motion detection circuit
60 CPU
62 normal image generation unit
64 computational image generation unit
66 computational processing time detection unit
68 frame adjustment unit
70 signal ratio calculation unit
72 correlation storage unit
74 oxygen saturation level calculation unit
76 image generation unit
78 isopleth 80 isopleth
82 graph
84 graph
86 camera
88 normal image
89 oxygen saturation image
90 delay-processed normal image
102 broadband light source
104 rotating filter
105 filter switch unit
108 inner filter
108a B1 filter
108b G filter
108c R filter
109 outer filter
109a B1 filter
109b B2 filter
109c G filter
109d R filter
204 blue laser light source
206 blue-green laser light source
210 fluorescent body
M movement of point of gaze
P point of gaze
t1, t2, t3 time

What is claimed is:

1. An endoscope system comprising:
a processor configured to function as:
an image obtaining unit that obtains a plurality of images obtained by radiating a plurality of types of illumination light in different wavelength ranges to a photographic subject to capture images of the photographic subject;
a computational image generation unit that generates a computational image by performing computational processing for at least one image among the plurality of images;
a normal image generation unit that generates a normal image by not performing the computational processing for at least one image among the plurality of images;
a computational processing time detection unit that detects a computational processing time taken to generate the computational image;
a motion detection unit that detects an amount of relative motion of the photographic subject;
a frame adjustment unit that makes a frame adjustment for changing the number of frames to be displayed per unit time for the normal image and/or the computational image; and
a display control unit that determines a display method for the normal image and the computational image subjected to the frame adjustment on the basis of the computational processing time and the amount of motion; and
a display that displays the normal image and the computational image in accordance with the display method,
wherein the frame adjustment is a process for decreasing the number of frames to be displayed per unit time for the normal image.

2. The endoscope system according to claim 1, wherein the display method is a method in which display of the normal image is delayed by the computational processing time.

3. The endoscope system according to claim 1, wherein the frame adjustment is a process for increasing the number of frames to be displayed per unit time for the computational image.

4. The endoscope system according to claim 1, wherein the frame adjustment is a process for increasing the number of frames to be displayed per unit time for the computational image by replicating the computational image.

5. The endoscope system according to claim 1, wherein the frame adjustment is a process for decreasing a difference between the number of frames to be displayed per unit time for the computational image and the number of frames to be displayed per unit time for the normal image.

6. The endoscope system according to claim 1, wherein the motion detection unit detects a relative motion vector of the photographic subject, and
the frame adjustment is a process for generating an interpolation frame for the computational image on the basis of the motion vector.

7. The endoscope system according to claim 1, wherein the computational image generation unit generates at least two computational images by using at least one image among the plurality of images twice or more in the computational processing.

8. The endoscope system according to claim 1, wherein the display method is a method in which
in a case where the amount of motion is equal to or larger than a threshold value, the normal image and the computational image are displayed in such a manner that a display area of the normal image is equal to or larger than a display area of the computational image, and
in a case where the amount of motion is smaller than the threshold value, the normal image and the computational image are displayed in such a manner that the display area of the computational image is equal to or larger than the display area of the normal image.

9. The endoscope system according to claim 1, wherein the display includes at least one monitor.

10. The endoscope system according to claim 1, wherein the display method is a method in which the computational image is superimposed on the normal image and displayed.

11. The endoscope system according to claim 1, wherein the display includes at least two monitors,
the monitors each comprise a line-of-sight detection device that detects a line of sight of an observer,
the line-of-sight detection device comprises a line-of-sight movement detector that detects a line-of-sight movement time taken for the movement of the line of sight, and
in a case where the line of sight of the observer moves from one of the monitors that displays the computational image to the other monitor that displays the normal image,
the display control unit determines the display method for the computational image and the normal image on the basis of the line-of-sight movement time.

12. The endoscope system according to claim 11, wherein the display method is a method in which display of the normal image is delayed by the line-of-sight movement time.

13. The endoscope system according to claim 1, wherein the computational processing is computational processing for generating an oxygen saturation image.

14. The endoscope system according to claim 1, wherein the computational processing is computational processing for generating a blood vessel highlight image.

15. An operation method for an endoscope system, the operation method comprising:
- a step of obtaining a plurality of images obtained by radiating a plurality of types of illumination light in different wavelength ranges to a photographic subject to capture images of the photographic subject;
- a step of generating a computational image by performing computational processing for at least one image among the plurality of images;
- a step of generating a normal image by not performing the computational processing for at least one image among the plurality of images;
- a step of detecting a computational processing time taken to generate the computational image;
- a step of detecting an amount of relative motion of the photographic subject;
- a step of making a frame adjustment for changing the number of frames to be displayed per unit time for the normal image and/or the computational image;
- a step of determining a display method for the normal image and the computational image subjected to the frame adjustment on the basis of the computational processing time and the amount of motion; and
- a step of displaying the normal image and the computational image on a display in accordance with the display method,
- wherein the frame adjustment is a process for decreasing the number of frames to be displayed per unit time for the normal image.

* * * * *